United States Patent
Stewart et al.

(10) Patent No.: US 10,405,766 B2
(45) Date of Patent: Sep. 10, 2019

(54) METHOD OF EXPLORING OR MAPPING INTERNAL CARDIAC STRUCTURES

(71) Applicant: Boston Scientific Scimed Inc., Maple Grove, MN (US)

(72) Inventors: Brian Stewart, North Reading, MA (US); Doron Harlev, Brookline, MA (US); Mordechai Perlman, Cambridge, MA (US); Paul Hultz, Brookline, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 105 days.

(21) Appl. No.: 15/275,439

(22) Filed: Sep. 25, 2016

(65) Prior Publication Data

US 2017/0086694 A1   Mar. 30, 2017

Related U.S. Application Data

(60) Provisional application No. 62/233,345, filed on Sep. 26, 2015.

(51) Int. Cl.
*A61B 5/044* (2006.01)
*A61B 5/042* (2006.01)
(Continued)

(52) U.S. Cl.
CPC .......... *A61B 5/044* (2013.01); *A61B 5/04012* (2013.01); *A61B 5/0422* (2013.01);
(Continued)

(58) Field of Classification Search
CPC . A61B 5/04012; A61B 5/0422; A61B 5/0452; A61B 5/044
See application file for complete search history.

(56) References Cited

U.S. PATENT DOCUMENTS

| 4,649,924 A | 3/1987 | Taccardi |
|---|---|---|
| 4,674,518 A | 6/1987 | Salo |

(Continued)

FOREIGN PATENT DOCUMENTS

| CN | 1253761 A | 5/2000 |
|---|---|---|
| CN | 101933803 A | 1/2011 |

(Continued)

OTHER PUBLICATIONS

International Search Report and Written Opinion issued in PCT/US2015/017289, dated May 6, 2015, 10 pages.

(Continued)

*Primary Examiner* — Tammie K Marlen
(74) *Attorney, Agent, or Firm* — Faegre Baker Daniels LLP

(57) ABSTRACT

Methods and systems for mapping and displaying cardiac structures are disclosed. The method includes sensing cardiac electrical signals at a plurality of points and generating a cardiac map of at least a portion of one or more cardiac structures based on at least a portion of the sensed cardiac electrical signals. A surface map having a corresponding first position relative to the cardiac map is generated. The surface map includes a first surface point, where a first cardiac electrical signal feature is represented on the surface map at the first surface point if a corresponding first cardiac electrical signal is sensed at a point that is located within a threshold distance of the first surface point. The cardiac map and the surface map, at the first position, are displayed. The surface map may be repositioned to a second position.

9 Claims, 7 Drawing Sheets

(51) Int. Cl.
*A61B 5/00* (2006.01)
*A61B 5/04* (2006.01)
*A61B 5/0452* (2006.01)

(52) U.S. Cl.
CPC .......... *A61B 5/0452* (2013.01); *A61B 5/6858* (2013.01); *A61B 5/7475* (2013.01); *A61B 2562/0209* (2013.01)

(56) References Cited

U.S. PATENT DOCUMENTS

| | | |
|---|---|---|
| 4,840,182 A | 6/1989 | Carlson |
| 4,920,490 A | 4/1990 | Isaacson |
| 5,156,151 A | 10/1992 | Imran |
| 5,284,142 A | 2/1994 | Goble et al. |
| 5,297,549 A | 3/1994 | Beatty et al. |
| 5,300,068 A | 4/1994 | Rosar et al. |
| 5,341,807 A | 8/1994 | Nardella |
| 5,381,333 A | 1/1995 | Isaacson et al. |
| 5,469,858 A | 11/1995 | Osborne |
| 5,480,422 A | 1/1996 | Ben-Haim |
| 5,483,968 A | 1/1996 | Adam et al. |
| 5,500,011 A | 3/1996 | Desai |
| 5,553,611 A | 9/1996 | Budd et al. |
| 5,568,809 A | 10/1996 | Ben-Haim |
| 5,577,502 A | 11/1996 | Darrow et al. |
| 5,588,429 A | 12/1996 | Isaacson et al. |
| 5,634,469 A | 6/1997 | Bruder et al. |
| 5,647,870 A | 7/1997 | Kordis et al. |
| 5,662,108 A | 9/1997 | Budd et al. |
| 5,687,737 A | 11/1997 | Branham et al. |
| 5,697,377 A | 12/1997 | Wittkampf |
| 5,704,365 A | 1/1998 | Albrecht et al. |
| 5,722,402 A | 3/1998 | Swanson et al. |
| 5,810,740 A | 9/1998 | Paisner |
| 5,840,025 A | 11/1998 | Ben-Haim |
| 5,840,031 A | 11/1998 | Crowley |
| 5,846,198 A | 12/1998 | Killmann |
| 5,848,972 A | 12/1998 | Triedman et al. |
| 5,876,336 A | 3/1999 | Swanson et al. |
| 5,921,982 A | 7/1999 | Lesh et al. |
| 5,954,665 A | 9/1999 | Ben-Haim |
| 5,971,933 A | 10/1999 | Gopakumaran et al. |
| 5,983,126 A | 11/1999 | Wittkampf |
| 6,014,581 A | 1/2000 | Whayne et al. |
| 6,050,267 A | 4/2000 | Nardella et al. |
| 6,070,094 A | 5/2000 | Swanson et al. |
| 6,095,150 A | 8/2000 | Panescu et al. |
| 6,167,296 A | 12/2000 | Shahidi |
| 6,226,542 B1 | 5/2001 | Reisfeld |
| 6,233,491 B1 | 5/2001 | Kordis et al. |
| 6,236,886 B1 | 5/2001 | Cherepenin et al. |
| 6,240,307 B1 | 5/2001 | Beatty et al. |
| 6,246,898 B1 | 6/2001 | Vesely et al. |
| 6,254,536 B1 | 7/2001 | DeVito |
| 6,278,894 B1 | 8/2001 | Salo et al. |
| 6,298,257 B1 | 10/2001 | Hall et al. |
| 6,301,496 B1 | 10/2001 | Reisfeld |
| 6,308,093 B1 | 10/2001 | Armoundas et al. |
| 6,314,310 B1 | 11/2001 | Ben-Haim et al. |
| 6,317,619 B1 | 11/2001 | Boernert et al. |
| 6,318,375 B1 | 11/2001 | Plicchi et al. |
| 6,360,123 B1 | 3/2002 | Kimchi et al. |
| 6,368,285 B1 | 4/2002 | Osadchy et al. |
| 6,400,981 B1 | 6/2002 | Govari |
| 6,490,474 B1 | 12/2002 | Willis et al. |
| 6,516,807 B1 | 2/2003 | Panescu et al. |
| 6,547,082 B1 | 4/2003 | Babini |
| 6,556,695 B1 | 4/2003 | Packer et al. |
| 6,574,492 B1 | 6/2003 | Ben-Haim et al. |
| 6,574,498 B1 | 6/2003 | Gilboa |
| 6,593,884 B1 | 7/2003 | Gilboa et al. |
| 6,600,948 B2 | 7/2003 | Ben-Haim et al. |
| 6,603,996 B1 | 8/2003 | Beatty et al. |
| 6,631,290 B1 | 10/2003 | Guck et al. |
| 6,640,119 B1 | 10/2003 | Budd et al. |
| 6,650,927 B1 | 11/2003 | Keidar |
| 6,690,963 B2 | 2/2004 | Ben-Haim et al. |
| 6,701,176 B1 | 3/2004 | Halperin et al. |
| 6,728,562 B1 | 4/2004 | Budd et al. |
| 6,735,465 B2 | 5/2004 | Panescu |
| 6,773,402 B2 | 8/2004 | Govari et al. |
| 6,807,439 B2 | 10/2004 | Edwards et al. |
| 6,839,588 B1 | 1/2005 | Rudy |
| 6,847,839 B2 | 1/2005 | Ciaccio et al. |
| 6,872,428 B2 | 3/2005 | Yang et al. |
| 6,892,090 B2 | 5/2005 | Verard et al. |
| 6,892,091 B1 | 5/2005 | Ben-Haim et al. |
| 6,893,588 B2 | 5/2005 | Lawson et al. |
| 6,939,309 B1 | 9/2005 | Beatty et al. |
| 6,941,166 B2 | 9/2005 | MacAdam et al. |
| 6,957,101 B2 | 10/2005 | Porath et al. |
| 6,978,168 B2 | 12/2005 | Beatty et al. |
| 6,984,207 B1 | 1/2006 | Sullivan et al. |
| 6,990,370 B1 | 1/2006 | Beatty et al. |
| 7,016,719 B2 | 3/2006 | Rudy et al. |
| 7,043,292 B2 | 5/2006 | Tarjan et al. |
| 7,136,694 B2 | 11/2006 | Hadley et al. |
| 7,263,397 B2 | 8/2007 | Hauck et al. |
| 7,505,810 B2 | 3/2009 | Harlev et al. |
| 7,515,954 B2 | 4/2009 | Harlev et al. |
| 7,628,757 B1 | 12/2009 | Koh |
| 7,629,981 B1 | 12/2009 | West |
| 7,729,752 B2 | 6/2010 | Harlev et al. |
| 8,103,338 B2 | 1/2012 | Harlev et al. |
| 8,137,343 B2 | 3/2012 | Harlev et al. |
| 8,208,991 B2 * | 6/2012 | Markowitz .......... A61B 5/0422 600/424 |
| 8,463,368 B2 | 6/2013 | Harlev et al. |
| 8,498,699 B2 | 7/2013 | Wells et al. |
| 8,571,647 B2 | 10/2013 | Harlev et al. |
| 8,744,566 B2 | 6/2014 | Harlev et al. |
| 8,768,440 B1 | 7/2014 | Brodnick et al. |
| 9,113,809 B2 | 8/2015 | Harlev et al. |
| 9,510,769 B2 | 12/2016 | Harlev et al. |
| 9,636,032 B2 | 5/2017 | Thakur et al. |
| 9,898,825 B2 | 2/2018 | Rivet-Sabourin |
| 2002/0065459 A1 | 5/2002 | MacAdam et al. |
| 2002/0151807 A1 | 10/2002 | Goldin |
| 2003/0018251 A1 | 1/2003 | Solomon |
| 2003/0065271 A1 | 4/2003 | Khoury |
| 2003/0076277 A1 | 4/2003 | Muramatsu et al. |
| 2003/0078509 A1 | 4/2003 | Panescu |
| 2003/0093067 A1 | 5/2003 | Panescu |
| 2003/0216630 A1 | 11/2003 | Jersey-Willuhn et al. |
| 2004/0059237 A1 | 3/2004 | Narayan et al. |
| 2004/0077942 A1 | 4/2004 | Hall et al. |
| 2004/0097806 A1 | 5/2004 | Hunter et al. |
| 2004/0158165 A1 | 8/2004 | Yonce et al. |
| 2004/0243015 A1 | 12/2004 | Smith et al. |
| 2004/0254437 A1 | 12/2004 | Hauck et al. |
| 2005/0037489 A1 | 2/2005 | Gepstein et al. |
| 2005/0038337 A1 | 2/2005 | Edwards |
| 2005/0054918 A1 | 3/2005 | Sra |
| 2005/0107834 A1 | 5/2005 | Freeman et al. |
| 2005/0154282 A1 | 7/2005 | Li et al. |
| 2005/0288599 A1 | 12/2005 | MacAdam et al. |
| 2006/0085049 A1 | 4/2006 | Cory et al. |
| 2006/0106375 A1 | 5/2006 | Werneth et al. |
| 2006/0116575 A1 | 6/2006 | Willis |
| 2006/0122526 A1 | 6/2006 | Berenfeld et al. |
| 2006/0173251 A1 | 8/2006 | Govari et al. |
| 2006/0178587 A1 | 8/2006 | Khoury |
| 2006/0241401 A1 | 10/2006 | Govari et al. |
| 2007/0016007 A1 | 1/2007 | Govari et al. |
| 2007/0038078 A1 | 2/2007 | Osadchy |
| 2007/0049821 A1 | 3/2007 | Willis |
| 2007/0112276 A1 | 5/2007 | Simms |
| 2007/0197929 A1 | 8/2007 | Porath et al. |
| 2007/0232949 A1 | 10/2007 | Saksena |
| 2007/0255588 A1 | 11/2007 | Hamilton |
| 2007/0265539 A1 | 11/2007 | Hastings et al. |
| 2007/0270688 A1 | 11/2007 | Gelbart et al. |
| 2007/0270703 A1 | 11/2007 | He et al. |

(56) References Cited

U.S. PATENT DOCUMENTS

| | | |
|---|---|---|
| 2007/0287902 A1 | 12/2007 | Fuimaono et al. |
| 2007/0299351 A1 | 12/2007 | Harlev et al. |
| 2007/0299352 A1 | 12/2007 | Harlev et al. |
| 2007/0299353 A1 | 12/2007 | Harlev et al. |
| 2008/0137934 A1 | 6/2008 | Sakaguchi et al. |
| 2008/0188765 A1 | 8/2008 | Stolarski et al. |
| 2008/0190438 A1 | 8/2008 | Harlev et al. |
| 2008/0221566 A1 | 9/2008 | Krishnan |
| 2008/0222109 A1 | 9/2008 | Sakurai |
| 2008/0234588 A1 | 9/2008 | Feldman et al. |
| 2008/0249424 A1 | 10/2008 | Harlev et al. |
| 2008/0269813 A1 | 10/2008 | Greenhut et al. |
| 2009/0171274 A1 | 7/2009 | Harlev et al. |
| 2009/0177072 A1 | 7/2009 | Harlev et al. |
| 2009/0253976 A1 | 10/2009 | Harlev et al. |
| 2009/0262979 A1 | 10/2009 | Markowitz et al. |
| 2009/0264741 A1 | 10/2009 | Markowitz et al. |
| 2009/0264777 A1 | 10/2009 | Markowitz et al. |
| 2010/0023082 A1 | 1/2010 | Dong et al. |
| 2010/0094274 A1 | 4/2010 | Narayan et al. |
| 2010/0268059 A1 | 10/2010 | Ryu et al. |
| 2010/0286551 A1 | 11/2010 | Harlev et al. |
| 2011/0098771 A1 | 4/2011 | Thakur et al. |
| 2011/0206256 A1 | 8/2011 | Ramanathan et al. |
| 2011/0251505 A1 | 10/2011 | Narayan et al. |
| 2011/0288605 A1 | 11/2011 | Kaib et al. |
| 2012/0029504 A1 | 2/2012 | Afonso et al. |
| 2012/0184858 A1 | 7/2012 | Harlev et al. |
| 2012/0184863 A1 | 7/2012 | Harlev et al. |
| 2012/0184865 A1 | 7/2012 | Harlev et al. |
| 2012/0191087 A1 | 7/2012 | Pachon Mateos et al. |
| 2012/0226110 A1 | 9/2012 | Markowitz et al. |
| 2013/0035576 A1 | 2/2013 | O'Grady et al. |
| 2013/0079645 A1 | 3/2013 | Amirana et al. |
| 2013/0274582 A1 | 10/2013 | Afonso et al. |
| 2013/0310702 A1 | 11/2013 | Reinders et al. |
| 2014/0052118 A1 | 2/2014 | Laske et al. |
| 2014/0073194 A1 | 3/2014 | Lim et al. |
| 2014/0200874 A1 | 7/2014 | Zeng et al. |
| 2014/0235986 A1 | 8/2014 | Harlev et al. |
| 2014/0330150 A1 | 11/2014 | Thakur et al. |
| 2014/0343388 A1 | 11/2014 | Thakur et al. |
| 2015/0254419 A1 | 9/2015 | Laughner et al. |
| 2015/0254893 A1 | 9/2015 | Laughner et al. |
| 2016/0012646 A1 | 1/2016 | Huang et al. |
| 2016/0051204 A1 | 2/2016 | Harlev et al. |
| 2016/0066814 A1 | 3/2016 | Markowitz et al. |
| 2016/0100770 A1 | 4/2016 | Afonso et al. |
| 2017/0189118 A1 | 7/2017 | Chopra et al. |
| 2017/0221262 A1 | 8/2017 | Laughner et al. |
| 2017/0311833 A1 | 11/2017 | Afonso et al. |

FOREIGN PATENT DOCUMENTS

| | | |
|---|---|---|
| CN | 102917638 A | 2/2013 |
| EP | 2204120 A1 | 7/2010 |
| EP | 2427106 A | 3/2012 |
| EP | 2485194 A2 | 8/2012 |
| WO | 1999005971 A1 | 2/1999 |
| WO | WO2006037172 A1 | 4/2006 |
| WO | 2006066324 A1 | 6/2006 |
| WO | 2007035306 A2 | 3/2007 |
| WO | 2007108776 A2 | 9/2007 |
| WO | 2007146864 A3 | 12/2007 |
| WO | 2008138009 A1 | 11/2008 |
| WO | 2010054320 A1 | 5/2010 |
| WO | 2010129095 A2 | 11/2010 |
| WO | WO2012037471 A2 | 3/2012 |
| WO | 2012092016 A1 | 7/2012 |
| WO | 2013006713 A2 | 1/2013 |
| WO | 2014185977 A1 | 11/2014 |
| WO | 2015130824 A1 | 9/2015 |
| WO | 2015134248 A1 | 9/2015 |

OTHER PUBLICATIONS

International Search Report and Written Opinion issued in PCT/US2015/017482, dated Jun. 2015, 9 pages.

Jain et al., "Cell Therapy Attenuates Deleterious Ventricular Remodeling and Improves Cardiac Performance after Myocardial Infarction", Circulation, 103:1920-1927, 2001.

Jalife, "Rotors and Spiral Waves in Atrial Fibrillation", Journal of Cardiovascular Electrophysiology, 14:776-780, 2003.

Jane et al., "Alignment Methods for Averaging of High-Resolution Cardiac Signals: A Comparative Study of Performance", IEEE Transactions on Biomedical Engineering, 38(6):571-579, 1991.

Japanese Office Action in JP Application No. 2009-515586, dated Jun. 26, 2012, 4 pages.

Jia et al., "Electrophysiologic Endocardial Mapping from a Noncontact Nonexpandable Catheter: A Validation Study of a Geometry-Based Concept". Journal of Cardiovascular Electrophysiology, 11:1238-1251, 2000.

Kikuchi et al., "Targeted Modification of Atrial Electrophysiology by Homogeneous Transmural Atrial Gene Transfer", Circulation, 111:264-270, 2005.

Kistler et al., "Validation of Three-Dimensional Cardiac Image Integration: Use of Integrated CT Image into Electroanatomic Mapping System to Performa Catheter Ablation of Atrial Fibrillation", Journal of Cardiovascular Electrophysiology, 17:341-348, 2006.

Kuklik et al., "The reconstruction, from a set of points, and analysis of the interior surface of the heart chamber", Physiol. Meas. 25:617-627, 2004.

Kun, Stevan et al., "Conductance Volumetric Model of An Eccentrically Positioned Catheter Within A Three-Compartment Ellipsoidal Ventricle", IEEE Transactions on Biomedical Engineering, vol. 40, No. 6, Jun. 1993, pp. 589-592.

L. Piegl, W. Tiller: The NURBS Book, 2nd Edition, Monographs in Visual Communication, Springer (1997).

Laciar et al., Improved Alignment Method for Noisy High-Resolution ECG and Holter Records Using a Multiscale Cross-Correlation, IEEE Transactions on Biomedical Engineering, 50(3), pp. 344-353, 2003.

Liu et al., "Endocardial Potential Mapping from a Noncontact Nonexpandable Catheter: A Feasibility Study", Annals of Biomedical Engineering, 26:994-1009, 1998.

Lorensen et al. "Marching Cubes: A High Resolution 3D Surface Construction Algorithm", Computer Graphics, 21(4):163-169, Jul. 1987.

Makela et al., "A Review of Cardiac Image Registration Methods", IEEE Transactions on Medical Imaging, 21(9):1011-1021, Sep. 2002.

Malladi R.et al "A Geometric Approach to Segmentation and Analysis of 3D Medical Images", Mathematical Methods in Biomedical Image Analysis, Proceedings of the Workshop on, Jun. 21-22, 1996, pp. 244-252.

Mangan, Alan et al., "Partitioning 3D Surface Meshes Using Watershed Segmentation", IEEE Transactions on Visualization and Computer Graphics, vol. 05, No. 4, pp. 308-321, (Oct.-Dec. 1999).

Meininger et al., "Initial Experience with a Novel Focused Ultrasound Ablation System for Ring Ablation Outside the Pulmonary Vein", Journal of Interventional Cardiac Electrophysiology, 8:141-148, 2003.

Merrill, Daniel R. et al., "Electrical stimulation of excitable tissue: design of efficacious and safe protocols", Journal of Neuroscience Methods, vol. 141, pp. 171-198 (2005).

Miller, "Editor's Forum—Application of Registration for Ablation: A Marriage of Technologies", Journal of Interventional Cardiac Electrophysiology, 11:87-89, 2004.

Nademanee et al., "A New Approach for Catheter Ablation of Atrial Fibrillation: Mapping of the Electrophysiologic Substrate", Journal of the American College of Cardiology, 43(11):2044-2053, 2004.

Non-final Office Action issued in U.S. Appl. No. 11/451,898, dated Sep. 25, 2008, 13 pages.

Non-final Office Action issued in U.S. Appl. No. 11/451,908, dated Sep. 4, 2008, 12 pages.

(56) References Cited

OTHER PUBLICATIONS

Noseworthy et al., "The Impact of Respiration on Left Atrial and Pulmonary Venous Anatomy: Implications for Image Guided Intervention", Heart Rhythm, 2(11), pp. 1173-1178, Nov. 2005.
Pappone et al., "Robotic Magnetic Navigation for Atrial Fibrillation Ablation", Journal of the American College of Cardiology, 47(7):1390-1400, 2006.
Paragios, "A Level Set Approach for Shape-Driven Segmentation and Tracking of the Left Ventricle", IEEE Transactions on Medical Imaging, 22(6):773-776, Jun. 2003.
Persson et al., "A Simple Mesh Generator in MATLAB", SIAM Review, 46(2):329-345, 2004.
Persson, "Mesh Generation for Implicit Geometrics", Massachusetts Institute of Technology—Thesis, Feb. 2005.
Pham, Dzung et al., "Current Methods in Medical Image Segmentation", Annu. Rev. Biomed. Eng., 02: pp. 315-337, (2000).
Rao et al., "Novel Noncontact Catheter System for Endocardial Electrical and Anatomical Imaging", Annals of Biomedical Engineering, 32(4):573-584, 2004.
Reddy et al., "Integration of Cardiac Magnetic Resonance Imaging With Three-Dimensional Electroanatomic Mapping to Guide Left Ventricular Catheter Manipulation—Feasibility in a Porcine Model of Healed Myocardial Infarction", Journal of the American College of Cardiology, 44(11):2202-2213, 2004.
Reddy et al., "Use of a Diode Laser Balloon Ablation Catheter To Generate Circumferential Pulmonary Venous Lesions in an Open-Thoracotomy Caprine Model", PACE, 27:52-57, 2004.
Sanders et al., "Spectral Analysis Identifies Sites of High-Frequency Activity Maintaining Atrial Fibrillation in Humans", Circulation, 112:789-797, 2005.
Sethian, "Level Set Methods and Fast Marching Methods: Evolving Interfaces in Computational Geometry, Fluid Mechanics, Computer Vision, and Materials Science", Department of Mathematics-University of California, Berkeley, Cambridge University Press, 1999.
Simon et al., "Electroanatomic Mapping of the Right Atrium With a Right Atrial Basket Catheter and Three-Dimensional Intracardiac Echocardiography", PACE, 27:318-326, 2004.
Smits et al., "Catheter-Based Intramyocarial Injection of Autologous Skeletal Myoblasts as a Primary Treatment of Ischemic Heart Failure", Journal of the American College of Cardiology, 42(12):2063-2069, 2003.
Solomon et al., "Real-Time Cardiac Catheter Navigation on Three-Dimensional CT Images", Journal of Interventional Cardiac Electrophysiology, 8:27-36, 2003.
Sra et al., "Registration of Three-Dimensional Left Atrial Computed Tomographic Images With Projection Images Obtained Using Fluoroscopy", Circulation, 112:3763-3768, 2005.
Sra, Jasbir et al, "Registration of 3D Computed Tomographic Images With Interventional Systems: Implications for Catheter Ablation of Atrial Fibrillation", J Intery Card Electrophysiol, 16:141-148, 2006.
Stevenson, "Radiofrequency Catheter Ablation of Ventricular Tachycardia After Myocardial Infarction", Circulation, 98:308-314, 1998.
Supplemental European Search Report issued in EP App[lication 10772414.8, dated May 7, 2013, 6 pages.
Supplemental European Search Report issued in EP Application No. 09824015, dated Jun. 1, 2012, 7 pages.
Supplementary European Search Report issued in EP Applicaion No. 09727423, dated May 15, 2012, 5 pages.
Supplementary European Search Report issued in EP Application No. 07798369.0 dated Jul. 30 2010, 6 pages.
Supplementary Europeant Search Report issued in EP Application No. 08728501, dated Feb. 25, 2011, 4 pages.
Taccardi et al., "A New Intracavitary Probe for Detecting the Site of the Origin of Ectopic Ventricular Beats During One Cardiac Cycle", Circulation, 75(1):272-281, 1987.
Thal et al., "Novel Applications in Catheter Ablation", Journal of Interventional Cardiac Electrophysiology, 13:17-21, 2005.
Thiagalingam et al., "Noncontact Mapping of the Left Ventricle: Insights from Validation With Transmural Contact Mapping", PACE, 27:570-578, 2004.
Voth, "The Inverse Problem of Electrocardiography: Industrial Solutions and Simulations", BEM and NFSI Conference Proceedings, Minneapolis, MN, May 12-15, 2005, pp. 191-194.
Wittkampf et al., "LocaLisa: New Technique for Real-Time 3-Dimensional Localization of Regular Intracardiac Electrodes", Circulation, 99:1312-1317, 1999.
Yezzi, Anthony et al., "A Geometric Snake Model for Segmentation of Medical Imagery", IEEE Transactions on Medical Imag, vol. 16, No. 2, Apr. 1997.
Andras Lasso et al., "SlicerWiki VolumeClip", Dec. 25, 2014, pp. 1-4, XP55332376, retrieved from teh internet: https://www.slicer.org/wiki/Documentation/4.4/Extensions/VolumeClip, retrieved on Jan. 5, 2017.
Anonymous: Solid Commands—Rhino 3-D Modeling (Rhinoceros 5), Sep. 17, 2015, XP055332631, Retrieved from Internet: http://docs.mcneel.com/rhino/6/help/en-us/seealso/sak_solidtools.htm, retrieved on Jan. 5, 2017, see under Cap, 2 pages.
International Search Report and Written Opinion issued in PCT/US2016/053613, dated Jan. 4, 2017, 11 pages.
International Search Report and Written Opinion issued in PCT/US2016/053630, dated Jan. 17, 2017, 12 pages.
International Search Report and Written Opinion issued in PCT/US2016/053633, dated Jan. 17, 2017, 14 pages.
Adams et al., "Seeded Region Growing", IEEE Transactions on Pattern Analysis and Machine Intelligence, 16(6):641-647, 1994.
Arthur et al., "Clinical Use of Intracardiac Impedance: Current Applications and Future Perspectives", PACE, vol. 24, No. 4, Part 1, Apr. 2001, pp. 500-506.
Baan, Jan et al., "Continuous Measurement of Left Ventricular Volume In Animals and Humans by Conductance Catheter", Diagnostic Methods-Conductance Catheter, Circulation, vol. 70, No. 5, 1984, pp. 812-823.
Badics et al., "Real-Time Reconstruction of Endocardial Potential Maps in Non-Contact Cardiac Mapping", International Journal for computation and Mathematics in Electrical and Electronic Engineering (COMPEL), vol. 28, No. 4, 2009.
Ben-Haim et al., "Nonfluoroscopic, in Vivo Navigation and Mapping Technology", Nature Medicine, 2(12):1393-1395, Dec. 1996.
Besl et al., "A Method for Registration of 3-D Shapes", IEEE Transactions on Pattern Analysis and Machine Intelligence, 14(2):239-256, Feb. 1992.
Blomstrom-Lundqvist et al., "ACC/AHA/ESC Guidelines for the Management of Patients With Supraventricular Arrhythmias-Executive Summary", Journal of the American College of Cardiology, 42(8):1493-1531, 2003.
Breithardt et al., "AHA Medical/Scientific Statement—Special Report: Standards for Analysis of Ventricular Late Potentials Using High-Resolution or Signal-Averaged Electrocardiography", Circulation, 83(4):1481-1488, Apr. 1991.
Brooks et al., "Electrical Imaging of the Heart", IEEE Signal Processing Magazine, pp. 24-42, 1997.
Buneo, Christopher A., Analyzing Neural Responses with Vector Fields, Journal of Neuroscience Methods, vol. 197, 2011, pp. 109-117.
Caspi et al., "Stem Cell Research: Regenerating the Heart Using Human Embryonic Stem Cells—from Cell to Bedside", IMAJ 8:208-214, 2006.
Cheney et al., "Electrical Impedance Tomography", SIAM Review 41(1):85-101, 1999.
Communication pursuant to Article 94(3) EPC issued in EP Application No. 07 798 369.0, dated Nov. 17, 2011, 5 pages.
De Groot et al., "Three-Dimensional Catheter Positioning During Radiofrequency Ablation in Patients: First Application of a Real-Time Position Management System", Journal of Cardiovascular Electrophysiology, 11(11):1183-1192, Nov. 2000.
Donahue et al., "Focal Modification of Electrical Conduction in the Heart by Viral Gene Transfer", Nature Medicine, 6(12):1395-1398, 2000.

(56) References Cited

OTHER PUBLICATIONS

Dong et al., "Integrated Electroanatomic Mapping With Three-Dimensional Computed Tomographic Images for Real-Time Guided Ablations", Circulation 113:186-194, 2006.
Durrer et al., "Total Excitation of the Isolated Human Heart", Circulation, vol. XLI, pp. 899-912, 1970.
E. J. Haug et al.: Design Sensitivity Analysis of Structural Systems, Mathematics in Science and Engineering, vol. 177 (1986).
Ector et al., "Cardiac Three-Dimensional Magnetic Resonance Imaging and Fluoroscopy Merging—A New Approach for Electroanatomic Mapping to Assist Catheter Ablation", Circulation, (Dec. 13, 2005), pp. 3769-3776.
Extended European Search Report issued in EP Application No. 10 772 414, dated May 7, 2013, 6 pages.
Fletcher, R. "Chapter 6: Sums of Squares and Nonlinear Equations," Practical Methods of Optimization, 2nd Edition, J. Willey & Sons, pp. 110-119 (1987).
Friedman, "Catheter Cryoablation of Cardiac Arrhythmias", Current Opinion in Cardiology, 20:48-54, 2005.
Friedman, "Novel Mapping Techniques for Cardiac Electrophysiology", Heart 2002, 87:575-582.
Geddes, L.A. et al., "Criteria for the Selection of Materials for Implanted Electrodes", Annals of Biomedical Engineering, vol. 31, pp. 879-890 (2003).
Gepstein et al., "A Novel Method for Nonfluoroscopic Catheter-Based Electroanatomical Mapping of the Heart", Circulation 95:1611-1622, 1997.
Gitosusastro et al., Performance Derivative Calculations and Optimization Process, IEEE Transactions on Magnetics, vol. 25, No. 4 (Jul. 1989) pp. 2834-2839.
Hansen: Rank-Deficient and Discrete III-Posed Problems: Numerical Aspects of Linear Inversion, SIAM, Philadelphia, USA, pp. 100-103, 1998.
He, Ye H. et al., "An Interactive Graphical System for Automated Mapping and Display of Cardiac Rhythms", Journal of Electrocardiology, vol. 32, No. 3, 1999, 17 pages.
He, Ye H., "An interactive graphical system for automated mapping and display of cardiac rhythms", Journal of Electrocardiology, vol. 32, No. 3, Jul. 1, 1999, pp. 225-241.
Holm, Magnus et al. A New Method for Analysis of Atrial Activation During Chronic Atrial Fibrillation in Man. IEEE Transactions on Biomedical Engineering, 43(2): 198-210, Feb. 1996.
Huang, Yi-Chih et al., "Development of a Third Generation Intraventricular Impedance Imaging (III) System: Evaluation of Hardware Design", Engineering in Medicine and Biology Society,. Proceedings of the 19th Annual International Conference of the IEEE, Oct. 30-Nov. 2, 1997 vol. 6, pp. 336-338 (1997).
International Preliminary Report on Patentability in PCT/US2007/070854, dated Dec. 16, 2008, 9 pages.
International Preliminary Report on Patentability in PCT/US2009/061277, dated May 3, 2011 11 pages.
International Preliminary Report on Patentability in PCT/US2010/027568 dated Oct. 25, 2011, 4 pages.
International Preliminary Report on Patentability issued in PCT/US2008/052385 dated Aug. 11, 2009, 6 pages.
International Preliminary Report on Patentability issued in PCT/US2009/036099, dated Oct. 14, 2010, 20 pages.
International Preliminary Report on Patentability issued in PCT/US2010/027436, dated Nov. 9, 2011, 4 pages.
International Preliminary Report on Patentability issued in PCT/US2014/000114, dated Nov. 26, 2015, 9 pages.
International Preliminary Report on Patentability issued in PCT/US2014/036939, dated Nov. 19, 2015, 8 pages.
International Preliminary Report on Patentability issued in PCT/US2015/0017289 dated Sep. 15, 2016, 8 pages.
International Preliminary Report on Patentability issued in PCT/US2015/017482 dated Sep. 15, 2016, 4 pages.
International Search Report and the Written Opinion in PCT/US08/52385 dated Aug. 8, 2008, 11 pages.
International Search Report and Written Opinion in PCT/US2010/027568, dated Nov. 4, 2010, 6 pages.
International Search Report and Written Opinion in PCT/US2012/020946, dated May 7, 2012, 15 pages.
International Search Report and Written Opinion issued in PCT/US2007/070854, dated Sep. 12, 2008, 10 pages.
International Search Report and Written Opinion issued in PCT/US2009/036099, dated Apr. 28, 2009, 21 pages.
International Search Report and Written Opinion issued in PCT/US2009/061277, dated Apr. 8, 2010, 12 pages.
International Search Report and Written Opinion issued in PCT/US2010/027436 dated Oct. 27, 2010, 10 pages.
International Search Report and Written Opinion issued in PCT/US2014/000114, dated Sep. 8, 2014, 12 pages.
International Search Report and Written Opinion issued in PCT/US2014/036939, dated Jul. 30, 2014, 11pages.

\* cited by examiner

METHOD OF EXPLORING OR MAPPING INTERNAL CARDIAC STRUCTURES

CROSS-REFERENCE TO RELATED APPLICATION

This application claims priority to Provisional Application No. 62/233,345, filed Sep. 26, 2015, which is herein incorporated by reference in its entirety.

TECHNICAL FIELD

The present disclosure generally relates to cardiac mapping systems and methods. More specifically, the present disclosure relates to cardiac mapping systems and methods for mapping and depicting internal cardiac structures.

BACKGROUND

Diagnosing and treating cardiac disorders often involve the introduction of a catheter into a cardiac chamber through the surrounding vasculature. The catheter has a plurality of sensors that sense electrical activity of the cardiac chamber. The electrical activity is generally processed into different maps including, but not limited to, voltage maps, activation maps and fractionation maps of the endocardial surface of the cardiac chamber. These maps are then used by a physician or other medical professional to treat and diagnose cardiac disorders.

These conventional maps, however, generally only show the electrical activity that occurs on the endocardial surface of the heart. As a result, structures that project inwardly from the endocardial surface typically are not depicted. Examples of structures that project inwardly from the endocardial surface include papillary muscles, septums and carinas. These structures may contribute to cardiac disorders. However, since the physician generally cannot view or analyze representations of these internal structures with conventional mapping technologies, the physician may find it more difficult to diagnose and treat disorders that may be associated with these internal structures.

SUMMARY

Embodiments of the subject matter disclosed herein include cardiac mapping systems that generate a cardiac map of cardiac tissue and a surface map. In embodiments, the surface map can include a surface point that is not located on the generated map. Additionally, a cardiac electrical signal feature sensed at a point that is located within a threshold distance of the surface point can be represented on the surface map at the surface point. In embodiments, the cardiac electrical signal feature represented at the surface point on the surface map may not be represented on the generated map. That is, in embodiments, a cardiac electrical signal feature that would otherwise not be displayed on the generated map can be displayed on the surface map. As such, a user of the cardiac mapping system can view representations of sensed electrical activity at points internal to and/or external to the generated map. Sensing electrical activity internal to the generated map may help a user in determining if an internal cardiac structure that is not represented on the generated map has contributed, or is contributing, to a cardiac disorder. Additionally, a user can use the cardiac mapping system to detect the boundaries of internal structures. In embodiments, a user can also reposition the surface map so that the surface map can include any number of different sets of surface points, and include corresponding cardiac electrical signal features sensed within threshold distances of the surface points, that are either internal to and/or external to the generated map.

In an Example 1, a method for mapping and displaying cardiac structures, the method comprises sensing, using a mapping probe, a plurality of cardiac electrical signal features at a plurality of points; generating, using a processing device, a cardiac map of at least a portion of one or more cardiac structures based on at least a portion of the plurality of cardiac electrical signal features; generating, using the processing device, a surface map having a corresponding first position relative to the cardiac map, the surface map comprises a first surface point, wherein a first cardiac electrical signal feature of the plurality of cardiac electrical signal features is represented on the surface map at the first surface point if the first cardiac electrical signal is sensed at a point that is located within a threshold distance of the first surface point; and displaying, on a display device, the cardiac map and the surface map at the first position.

In an Example 2, the method according to Example 1, wherein the first surface point is not located on the generated map.

In an Example 3, the method according to either Example 1 or 2, wherein the cardiac electrical signal feature is not represented on the generated map.

In an Example 4, the method according to any one of Examples 1-3, wherein the surface map is a plane map.

In an Example 5, the method according to any one of Examples 1-4, further comprises repositioning the surface map so that the repositioned surface map has a corresponding second position relative to the generated map, the repositioned surface map comprises a second surface point, wherein a second cardiac electrical signal feature of the plurality of cardiac electrical signal features is represented on the repositioned surface map at the second surface point if the second cardiac electrical signal feature is sensed at a point that is located within the threshold distance of the second surface point; and displaying, on the display device, the repositioned surface map at the second position.

In an Example 6, the method according to Example 5, further comprises: performing less than all of a plurality of display enhancing functions to the displayed repositioned surface map if the displayed repositioned surface map is being viewed in a quick-view mode.

In an Example 7, the method according to any of Examples 1-6, wherein the respective cardiac electrical signal feature comprises at least one of an activation time, a minimum voltage value, a maximum voltages value, a maximum negative time-derivative of voltage, an instantaneous potential, a voltage amplitude, a dominant frequency, a peak-to-peak voltage.

In an Example 8, the method according to any of Examples 1-7, wherein the surface map passes through a papillary muscle or a septum of the one or more cardiac structures.

In an Example 9, a mapping system comprises: a mapping probe comprising a plurality of electrodes located on a distal end of the cardiac mapping probe, wherein each of the plurality of electrodes is configured to sense a plurality of cardiac electrical signal features of a cardiac structure at a plurality of points; a processing device configured to: generate a cardiac map of at least a portion of the one or more cardiac structures based on at least a portion of the plurality of cardiac electrical signal features; generate a surface map having a corresponding first position relative to the generated map, the surface map comprising a first surface point, wherein a first cardiac electrical signal feature of the plurality of cardiac electrical signal features is represented on the surface map at the first surface point if the first cardiac electrical signal feature is sensed at a point that is located within a threshold distance of the first surface point; and output to a display device the generated map and the generated surface map at the first position; and the display device configured to display the generated map and the generated surface map at the first position.

In an Example 10, the cardiac mapping system according to Example 9, wherein the first surface point is not located on the generated map.

In an Example 11, the cardiac mapping system according to either Examples 9 or 10, wherein the cardiac electrical signal feature is not represented on the generated map.

In an Example 12, the cardiac mapping system according to any of Examples 9-11, the cardiac mapping system further comprises: a user input device; wherein the processing device is further configured to: reposition the surface map, in response to a user input received by the user input device, so that the repositioned surface map has a corresponding second position relative to the generated map, the repositioned surface map comprising a second surface point, wherein a second cardiac electrical signal feature of the plurality of cardiac electrical signal features is represented on the repositioned surface map at the second surface point if the second cardiac electrical signal feature is sensed at a point that is located within the threshold distance of the second surface point; and output the repositioned surface map at the second position to the display device.

In an Example 13, the cardiac mapping system according to Example 12, wherein the processing device is further configured to: perform less than all of a plurality of display enhancing functions to the displayed repositioned surface map if the displayed repositioned surface map is being viewed in a quick-view mode.

In an Example 14, the cardiac mapping system according to any of Examples 9-13, wherein the respective cardiac electrical signal feature comprises at least one of an activation time, a minimum voltage value, a maximum voltages value, a maximum negative time-derivative of voltage, an instantaneous potential, a voltage amplitude, a dominant frequency, a peak-to-peak voltage.

In an Example 15, the cardiac mapping system according to any of Examples 9-14, wherein the surface map passes through a papillary muscle or a septum of the one or more cardiac structures.

In an Example 16, a method for mapping and displaying internal cardiac structures, the method comprises: sensing, using a mapping probe, a plurality of cardiac electrical signal features at a plurality of points; generating, using a processing device, a cardiac map of at least a portion of one or more cardiac structures based on at least a portion of the plurality of cardiac electrical signal features; generating, using the processing device, a surface map having a corresponding first position relative to the cardiac map, the surface map comprising a first surface point, wherein a first cardiac electrical signal feature of the plurality of cardiac electrical signal features is represented on the surface map at the first surface point if the first cardiac electrical signal feature is sensed at a point that is located within a threshold distance of the first surface point; and displaying, on a display device, the generated map and the generated surface map at the first position.

In an Example 17, the method of Example 16, wherein the first surface point is not located on the generated map.

In an Example 18, the method of Example 16, wherein the cardiac electrical signal feature is not represented on the generated map.

In an Example 19, the method of Example 16, wherein the surface map is a plane map.

In an Example 20, the method of Example 16, further comprises: repositioning the surface map so that the repositioned surface map has a corresponding second position relative to the generated map, the repositioned surface map comprising a second surface point, wherein a second cardiac electrical signal feature of the plurality of cardiac electrical signal features is represented on the repositioned surface map at the second surface point if the second cardiac electrical signal feature is sensed at a point that is located within the threshold distance of the second surface point; and displaying, on the display device, the repositioned surface map at the second position.

In an Example 21, the method of Example 20, further comprises: performing less than all of a plurality of display enhancing functions to the displayed repositioned surface map if the displayed repositioned surface map is being viewed in a quick-view mode.

In an Example 22, the method of Example 16, wherein the respective cardiac electrical signal feature comprises at least one of an activation time, a minimum voltage value, a maximum voltages value, a maximum negative time-derivative of voltage, an instantaneous potential, a voltage amplitude, a dominant frequency, a peak-to-peak voltage.

In an Example 23, the method of Example 16, wherein the surface map passes through a papillary muscle or a septum of the one or more cardiac structures.

In an Example 24, a mapping system comprises: a mapping probe comprising a plurality of electrodes located on a distal end of the cardiac mapping probe, wherein each of the plurality of electrodes is configured to sense a plurality of cardiac electrical signal features of a cardiac structure at a plurality of points; a processing device configured to: generate a cardiac map of at least a portion of one or more cardiac structures based on at least a portion of the plurality of cardiac electrical signal features; generate a surface map having a corresponding first position relative to the generated map, the surface map comprising a first surface point, wherein a first cardiac electrical signal feature of the plurality of cardiac electrical signal features is represented on the surface map at the first surface point if the first cardiac electrical signal feature is sensed at a point that is located within a threshold distance of the first surface point; and output to a display device the generated map and the generated surface map at the first position; and the display device configured to display the generated map and the generated surface map at the first position.

In an Example 25, the cardiac mapping system of Example 24, wherein the first surface point is not located on the generated map.

In an Example 26, the cardiac mapping system of Example 24, wherein the cardiac electrical signal feature is not represented on the generated map.

In an Example 27, the cardiac mapping system of Example 24, wherein the surface map is a plane map.

In an Example 28, the cardiac mapping system of Example 24, the cardiac mapping system further comprises: a user input device; wherein the processing device is further configured to: reposition the surface map, in response to a user input received by the user input device, so that the repositioned surface map has a corresponding second position relative to the generated map, the repositioned surface map comprising a second surface point, wherein a second cardiac electrical signal feature of the plurality of cardiac electrical signal features is represented on the repositioned surface map at the second surface point if the second cardiac electrical signal feature is sensed at a point that is located within the threshold distance of the second surface point; and the display device configured to display the repositioned surface map.

In an Example 29, the cardiac mapping system of Example 28, wherein the processing device is further configured to: perform less than all of a plurality of display enhancing functions to the displayed repositioned surface map if the displayed repositioned surface map is being viewed in a quick-view mode.

In an Example 30, the cardiac mapping system of Example 24, wherein the respective cardiac electrical signal feature comprises at least one of an activation time, a minimum voltage value, a maximum voltages value, a maximum negative time-derivative of voltage, an instantaneous potential, a voltage amplitude, a dominant frequency, a peak-to-peak voltage.

In an Example 31, the cardiac mapping system of Example 24, wherein the surface map passes through a papillary muscle or an extended septum of the one or more cardiac structures.

In an Example 32, one or more computer-readable media having computer-executable instructions embodied thereon that, when executed by a processor, cause the processor to: generate a cardiac map of at least a portion of the one or more cardiac structures based on at least a portion of a plurality of cardiac electrical signal features; generate a surface map having a corresponding first position relative to the cardiac map, the surface map comprising a first surface point, wherein a first cardiac electrical signal feature of the plurality of cardiac electrical signal features is represented on the surface map at the first surface point if the first cardiac electrical signal feature is sensed at a point that is located within a threshold distance of the first surface point; and output to a display device the generated map and the generated surface map at the first position.

In an Example 33, the media of Example 32, wherein the first surface point is not located on the generated map.

In an Example 34, the media of Example 32, further comprising instructions that cause the processor to: reposition the surface map, in response to a user input received by the user input device, so that the repositioned surface map has a corresponding second position relative to the generated map, the repositioned surface map comprising a second surface point, wherein a second cardiac electrical signal feature of the plurality of cardiac electrical signal features is represented on the repositioned surface map at the second surface point if the second cardiac electrical signal feature is sensed at a point that is located within the threshold distance of the second surface point; and output the repositioned surface map at the second position to the display device.

In an Example 35, the media of Example 34, further comprises: perform less than all of a plurality of display enhancing functions to the displayed repositioned surface map if the displayed repositioned surface map is being viewed in a quick-view mode.

Figure 1:
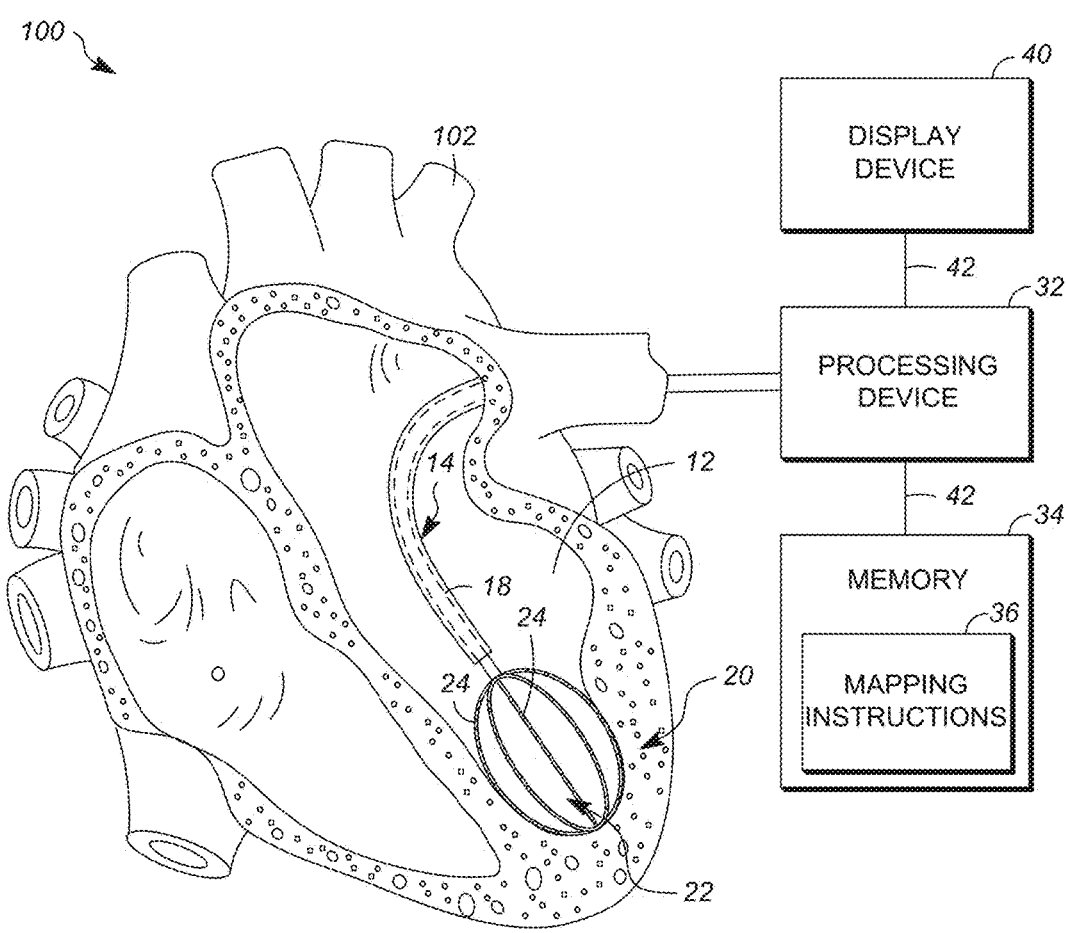
FIG. 1 is a schematic view of a system for mapping and displaying cardiac structures, in accordance with embodiments of the present disclosure.

While the disclosed subject matter is amenable to various modifications and alternative forms, specific embodiments have been shown by way of example in the drawings and are described in detail below. The intention, however, is not to limit the disclosure to the particular embodiments described. On the contrary, the disclosure is intended to cover all modifications, equivalents, and alternatives falling within the scope of the disclosure as defined by the appended claims.

Although the term "block" may be used herein to connote different elements illustratively employed, the term should not be interpreted as implying any requirement of, or particular order among or between, various steps disclosed herein unless and except when explicitly referring to the order of individual steps.

DETAILED DESCRIPTION

FIG. 1 is a schematic view of a mapping system 100 for mapping cardiac structures 102, in accordance with embodiments of the disclosure. Throughout this disclosure, the term "cardiac structure" can mean any portion of a subject's heart and/or adjacent features such as, for example, an endocardium, an epicardium, an entire heart, a heart chamber, a portion of a heart chamber, a valve, a coronary sinus and/or its tributaries, a portion of a coronary sinus and/or a portion of its tributaries, a pulmonary artery, other surrounding vasculature and/or the like. While this disclosure discusses using the cardiac mapping system to map cardiac structures 102, embodiments of the cardiac mapping system 100 can also, or alternatively, be used to map other organs and biological tissue including, but not limited to, kidneys, lungs, brains, gall bladders, livers, spleens and intestines.

The system 100 includes a mapping probe 14. The mapping probe 14 includes a flexible catheter body 18. When mapping cardiac structures 102, a physician or medical professional inserts the distal end of the catheter body 18 into a cardiac chamber (e.g., the left ventricle of the heart) of a patient. While the left ventricle of the heart is shown, alternatively, the distal end of the catheter body 18 can be deployed in other parts of the heart and/or surrounding vasculature, such as, e.g., the left atrium, the right atrium, or the right ventricle, the coronary sinus and its tributaries and the pulmonary artery. The distal end of the catheter body 18 has a multiple electrode structure 20. In the illustrated embodiment, the electrode structure 20 takes the form of a basket defining an open interior space 22. While the electrode structure 20 takes the form of a basket in the illustrated embodiment, this is only an example and other electrode structures can be utilized. For example, the electrode structure may include one or more electrodes (e.g., ablation electrodes, microelectrodes, ring electrodes, etc.) disposed on an ablation catheter, a diagnostic catheter, and/or the like.

As shown in FIG. 1, the electrode structure 20 includes a number of electrodes 24. The electrodes 24 are configured to sense cardiac electrical signals traversing a cardiac structure 102. The cardiac electrical signals can be sensed, for example, on the endocardial surface of the heart and/or in the heart chamber below the endocardial surface. As used herein, a mapped representation of a cardiac electrical signal feature that is sensed at a point inside a heart chamber is referred to as being below the endocardial surface. That is, for example, because the cardiac map includes an anatomical shell that represents an endocardial surface and, from the perspective of the viewer, a point that is located inside the chamber, and not on the endocardial surface, would appear to be "below" the mapped surface.

As the term is used herein, a sensed cardiac electrical signal may refer to one or more sensed signals. Each cardiac electrical signal may include a number of intracardiac electrograms (EGMs) sensed within a patient's heart, and may include any number of features that may be ascertained by aspects of the system 100. Examples of cardiac electrical signal features include, but are not limited to, activation times, minimum voltage values, maximum voltages values, maximum negative time-derivatives of voltages, instantaneous potentials, voltage amplitudes, dominant frequencies, peak-to-peak voltages, and/or the like. A cardiac electrical signal feature may refer to one or more features extracted from one or more cardiac electrical signals, derived from one or more features that are extracted from one or more cardiac electrical signals, and/or the like. Additionally, a representation, on a cardiac and/or a surface map, of a cardiac electrical signal feature may represent one or more cardiac electrical signal features, an interpolation of a number of cardiac electrical signal features, and/or the like.

Each cardiac signal also may be associated with a set of respective position coordinates that corresponds to the location at which the cardiac electrical signal was sensed. Each of the respective position coordinates for the sensed cardiac signals may include three-dimensional Cartesian coordinates, polar coordinates, and/or the like. In embodiments, other coordinate systems can be used. In embodiments, an arbitrary origin is used and the respective position coordinates refer to positions in space relative to the arbitrary origin. Since, in embodiments, the cardiac signals may be sensed on the endocardial surface as well as in the chamber enclosed by the endocardial surface, the respective position coordinates may be on the endocardial surface of the patient's heart and/or below the endocardial surface.

The electrodes 24 are electrically coupled to a processing device 32. That is, each electrode 24 on the basket structure 20 may be communicatively coupled to the processing device 32, via a wired and/or wireless connection. In embodiments where there is a wired connection, the wires (not shown) from each electrode may extend through the catheter body 18 of the cardiac mapping probe 14 and electrically couple each electrode 24 to the processing device 32. In embodiments where there is a wireless connection, a transmitter (not shown) may be included in the cardiac mapping probe 14 which may transmit sensed signals from each electrode 24 on the basket structure 20 to a receiver (not shown) that is coupled to the processing device 32.

Once the sensed signals are received by the processing device 32 from the electrodes 24, the processing device 32 processes the sensed signals. The processing device 32 processes the sensed signals according to mapping instructions 36, which are stored on memory 34. The processing device 32 may be, include, or be included in, an electrical processor, a software processor, a general purpose microprocessor and/or a special purpose microprocessor, and may include a sole processor or one of multiple processors or cores. The processed signals are displayed on a display device 40. The display device 40 can include, but is not limited to, one of the following display devices: a cathode ray tube (CRT) display, a light emitting diode (LED) display, or a liquid crystal display (LCD) display.

The memory 34 can be in the form of volatile and/or nonvolatile memory and may be removable, nonremovable, or a combination thereof. Media examples include Random Access Memory (RAM); Read Only Memory (ROM); Electronically Erasable Programmable Read Only Memory (EEPROM); flash memory; optical or holographic media; magnetic cassettes, magnetic tape, magnetic disk storage or other magnetic storage devices; data transmissions; and/or any other medium that can be used to store information and can be accessed by a processing device 32 such as, for example, quantum state memory, and/or the like. Mapping instructions 36 may be programmed on the memory 34 using any number of different programming environments, including various languages, development kits, frameworks, and/or the like. Some or all of the functionality contemplated herein may also, or alternatively, be implemented in hardware and/or firmware.

The processing device 32, the memory 34 and the display device 40 can be coupled together, directly and/or indirectly, by a bus 42. Any number of additional components, different components, and/or combinations of components may also be coupled to the processing device 32, memory 34 and display device 40, via the bus 42. The bus represents what may be one or more busses (such as, for example, an address bus, data bus, or combination thereof).

The illustrative mapping system 100 shown in FIG. 1 is not intended to suggest any limitation as to the scope of use or functionality of embodiments of the present disclosure. Neither should the illustrative mapping system 100 be interpreted as having any dependency or requirement related to any single component or combination of components illustrated therein. Additionally, various components depicted in FIG. 1 may be, in embodiments, integrated with various ones of the other components depicted therein (and/or components not illustrated), all of which are considered to be within the ambit of the present disclosure. For example, the memory 34 may be integrated with the processing device 32.

Figure 2:
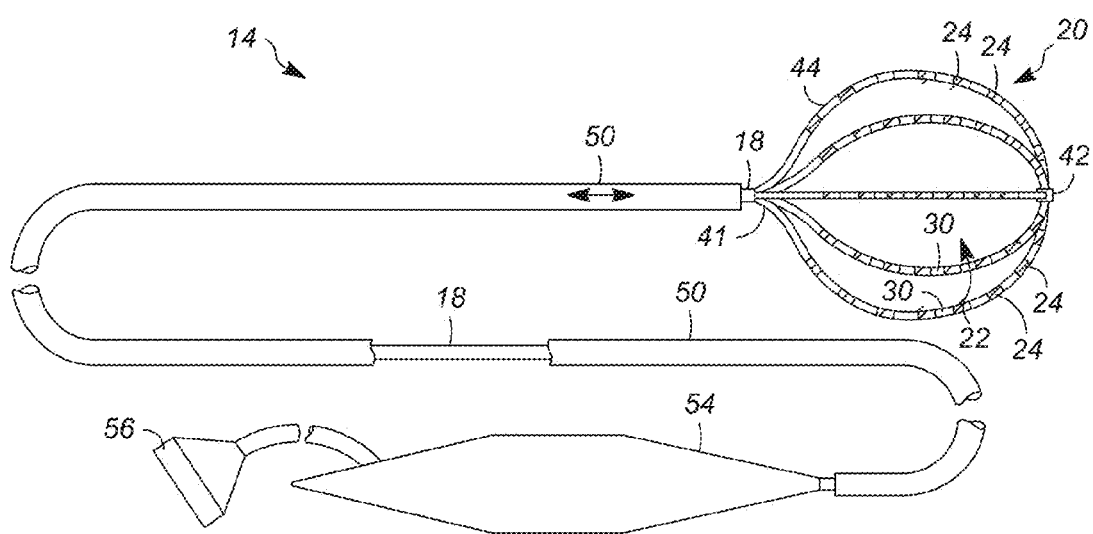
FIG. 2 is a schematic view of a mapping probe for use in association with the system of FIG. 1, in accordance with embodiments of the present disclosure.

FIG. 2 is a schematic view of a mapping probe 14 for use in association with the system 100 of FIG. 1, in accordance with embodiments of the disclosure. The mapping probe 14 has a flexible catheter body 18, the distal end of which carries the three-dimensional basket structure 20 that includes the mapping electrodes 24. As stated above, the mapping electrodes 24 sense signals in a cardiac structure; and the sensed signals are sent to a processing device 32, via a wired and/or wireless connection. The processing device 32 processes the sensed signals and a cardiac map is created, as described, for example, in the description corresponding to FIG. 3, below. The types of cardiac maps created can include, but are not limited to, the following: a voltage map, an activation map, a fractionation map, a velocity map, and/or the like.

The basket structure 20 comprises a base member 41 and an end cap 42 between which flexible splines 44 generally extend in a circumferentially spaced relationship. As discussed above, the basket structure 20 takes the form of a basket defining an open interior space 22. In embodiments, the splines 44 are made of a resilient inert material, such as Nitinol metal or silicone rubber, and are connected between the base member 41 and the end cap 42 in a resilient, pre-tensed condition, to bend and conform to the tissue surface they contact. In the illustrated embodiments, eight splines 44 form the three-dimensional structure 20. Additional or fewer splines 44 could be used in other embodiments, and the three-dimensional structure 20 may be configured according to any number of different shapes such as, for example, generally spherical shapes, generally elliptical shapes, generally tear-drop shapes, and/or the like. As illustrated, each spline 44 carries eight mapping electrodes 24. Additional or fewer mapping electrodes 24 could be disposed on each spline 44 in other embodiments of the three-dimensional structure 20. In the illustrated embodiments, the three-dimensional structure 20 is relatively small (e.g., 40 mm or less in diameter). In embodiments, the three-dimensional structure 20 is larger (e.g., 40 mm in diameter or greater).

In embodiments, a slidable sheath 50 is movable along the major axis of the catheter body 30. Moving the sheath 50 forward (i.e., toward the distal end) causes the sheath 50 to move over the three-dimensional structure 20, thereby collapsing the structure 20 into a compact, low profile condition suitable for introduction into an interior space, such as, for example, into the heart. In contrast, moving the sheath 50 rearward (i.e., toward the proximal end) exposes the three-dimensional structure 20, allowing the structure 20 to elastically expand and assume the pre-tensed position illustrated in FIG. 2. Further details of embodiments of the three-dimensional structure 20 are disclosed, for example, in U.S. Pat. No. 5,647,870, entitled "Multiple Electrode Support Structures," which is hereby incorporated by reference in its entirety.

In embodiments where the mapping probe 14 uses a wired connection, a signal wire (not shown) may be electrically coupled to each mapping electrode 24. The wires may extend through the body 30 of the mapping catheter 20 into a handle 54, in which they may be coupled to an external connector 56, which may be, for example, a multiple pin connector. The connector 56 electrically couples the mapping electrodes 24 to the processing system 32. Further details on mapping systems and methods for processing signal generated by mapping catheters are discussed, for example, in U.S. Pat. No. 6,070,094, entitled "Systems and Methods for Guiding Movable Electrode Elements within Multiple-Electrode Structure;" U.S. Pat. No. 6,233,491, entitled "Cardiac Mapping and Ablation Systems;" and U.S. Pat. No. 6,735,465, entitled "Systems and Processes for Refining a Registered Map of a Body Cavity," the disclosures of which are incorporated herein by reference.

It is noted that other electrode structures could be deployed on the distal end of a mapping catheter. It is further noted that the multiple mapping electrodes 24 may be disposed on more than one structure, rather than, for example, the single mapping probe 14 illustrated in FIG. 2. For example, if mapping within the left atrium with multiple mapping structures, an arrangement comprising a coronary sinus catheter carrying multiple mapping electrodes and a basket catheter carrying multiple mapping electrodes positioned in the left atrium may be used. As another example, if mapping within the right atrium with multiple mapping structures, an arrangement comprising a decapolar catheter carrying multiple mapping electrodes for positioning in the coronary sinus, and a loop catheter carrying multiple mapping electrodes for positioning around the tricuspid annulus may be used.

Although the mapping electrodes 24 have been described as being carried by dedicated mapping probes, such as the mapping probe 14, the mapping electrodes may be carried on non-mapping dedicated probes or multifunction probes. For example, an ablation catheter can be configured to include one or more mapping electrodes 24 disposed on the distal end of the catheter body and coupled to the signal processing system 32.

Figure 3:
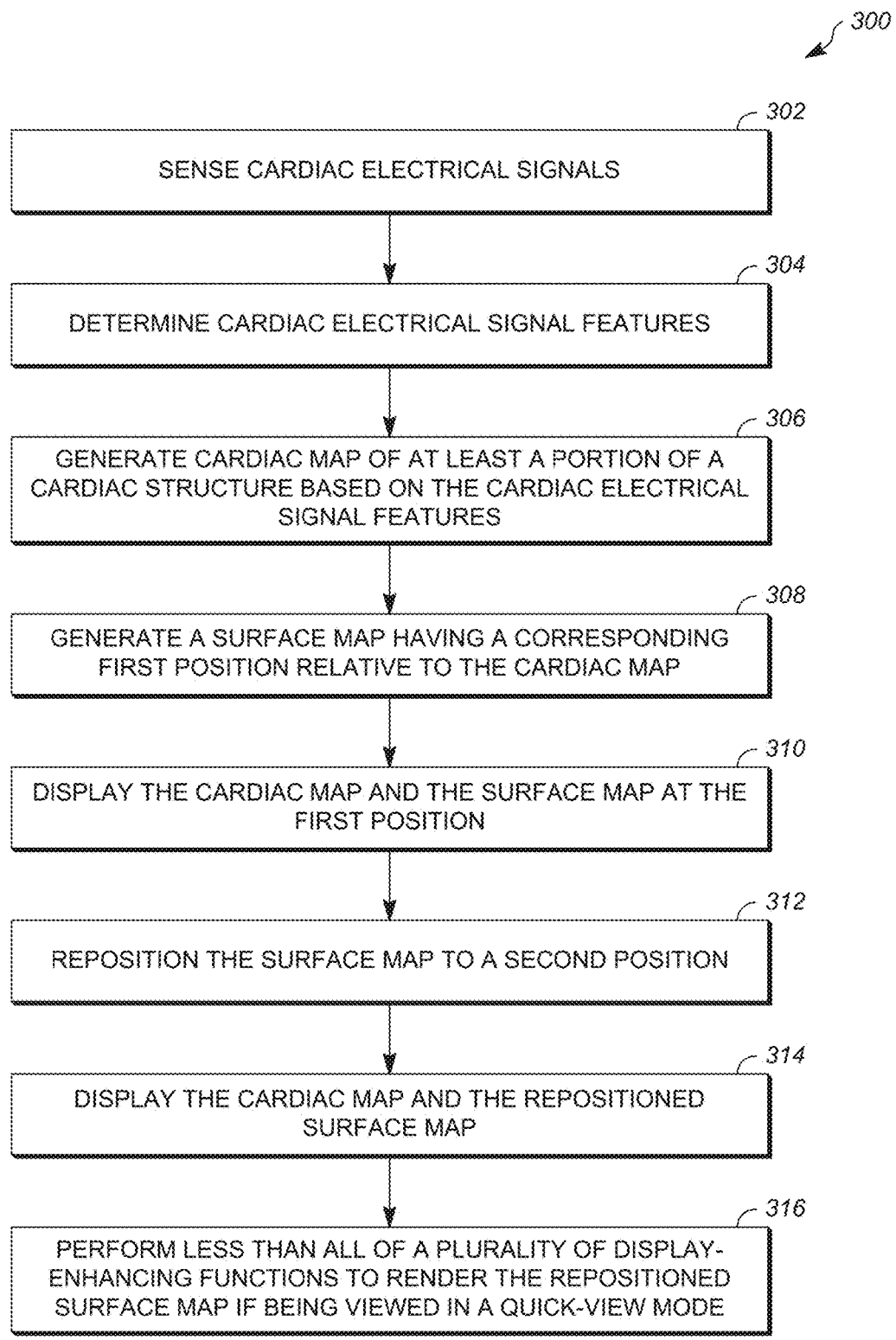
FIG. 3 is a flow diagram depicting a method for mapping and displaying cardiac structures, in accordance with embodiments of the present disclosure.

FIG. 3 is a flow diagram depicting an illustrative method 300 for mapping and viewing cardiac structures, in accordance with embodiments of the disclosure. Embodiments of method 300 may be performed, in whole or in part, by a mapping system (e.g., the mapping system 100 depicted in FIG. 1). Embodiments of the method 300 include sensing, using a mapping probe, a number of cardiac electrical signals of a cardiac structure at a number of points (block 302) and determining one or more features of each of the sensed cardiac signals (block 304). Each of the sensed cardiac electrical signals (and, accordingly, features of each signal) corresponds to a respective point (e.g., location in space) where the cardiac electrical signal was sensed. In embodiments, the mapping probe can have the same or similar characteristics to the mapping probe 14 described above in FIGS. 1 and 2.

The respective cardiac electrical signals can include a number of intracardiac EGMs. Examples of features of the cardiac electrical signals include, but are not limited to, activation times, minimum voltage values, maximum voltages values, maximum negative time-derivatives of voltages, instantaneous potentials, voltage amplitudes, dominant frequencies, peak-to-peak voltages, and/or the like. Each of the respective points at which a cardiac electrical signal is sensed has a corresponding set of three-dimensional position coordinates. For example, the position coordinates of the points may be represented in Cartesian coordinates. Other coordinate systems can be used, as well. In embodiments, an arbitrary origin is used and the respective position coordinates are defined with respect to the arbitrary origin. In some embodiments, the points have non-uniform spacing, while in other embodiments, the points have uniform spacing. In embodiments, the point corresponding to each sensed cardiac electrical signal may be located on the endocardial surface of the heart and/or below the endocardial surface of the heart.

Embodiments of the method 300 also include generating a cardiac map of at least a portion of one or more cardiac structures (block 306). In embodiments, the cardiac map may be generated based, at least in part, on the cardiac electrical signal features. In embodiments, the cardiac map may also be generated, at least in part, using any number of other signals, techniques, and/or the like. For example, embodiments may utilize impedance mapping techniques to generate one or more portions of the cardiac map such as, for example, an anatomical shell upon which electrical signal features are represented. In embodiments, a surface may be fitted on one or more of the points associated with the cardiac electrical signals to generate a shell representing the endocardial surface of the one or more cardiac structures. In embodiments, a surface may also be fitted on one or more of the points associated with the cardiac electrical signals to generate a shell representing an epicardium surface or other excitable cardiac tissue. In embodiments, one or more of the cardiac electrical signal features at the corresponding points can be included on the shell to generate a cardiac map of the one or more cardiac structures. For example, embodiments may include displaying annotations on the cardiac map that represent features, extracted from the cardiac electrical signals and/or derived from other features, such as, for example, activation times, minimum voltage values, maximum voltages values, maximum negative time-derivatives of voltages, instantaneous potentials, voltage amplitudes, dominant frequencies, peak-to-peak voltages, and/or the like.

Embodiments of the method 300 further include generating a surface map having a corresponding first position relative to the cardiac map, wherein the surface map includes a first surface point (block 308). The surface map may include any type of surface such as, for example, a planar surface, a curved surface, a folded surface, a twisted surface, an open surface, a closed surface, and/or the like. In embodiments, for example, the surface may be a surface of a three-dimensional object such as a cube, a sphere, a pyramid, and/or the like. Examples of a planar surface include a polygon (e.g., a triangle, a quadrilateral, a rectangle, a square, an ellipsoid, a pentagon, a hexagon, and/or the like), an irregular shape, and/or the like. An example quadrilateral is shown in FIGS. 4A-4D. In embodiments, more than one surface map may be generated, where each additional surface map may have a corresponding position that is different than the first position. In embodiments, one or more surface maps may be defined according to different characteristics, manipulated separately or in a synchronized manner, and/or the like.

Figure 4A:
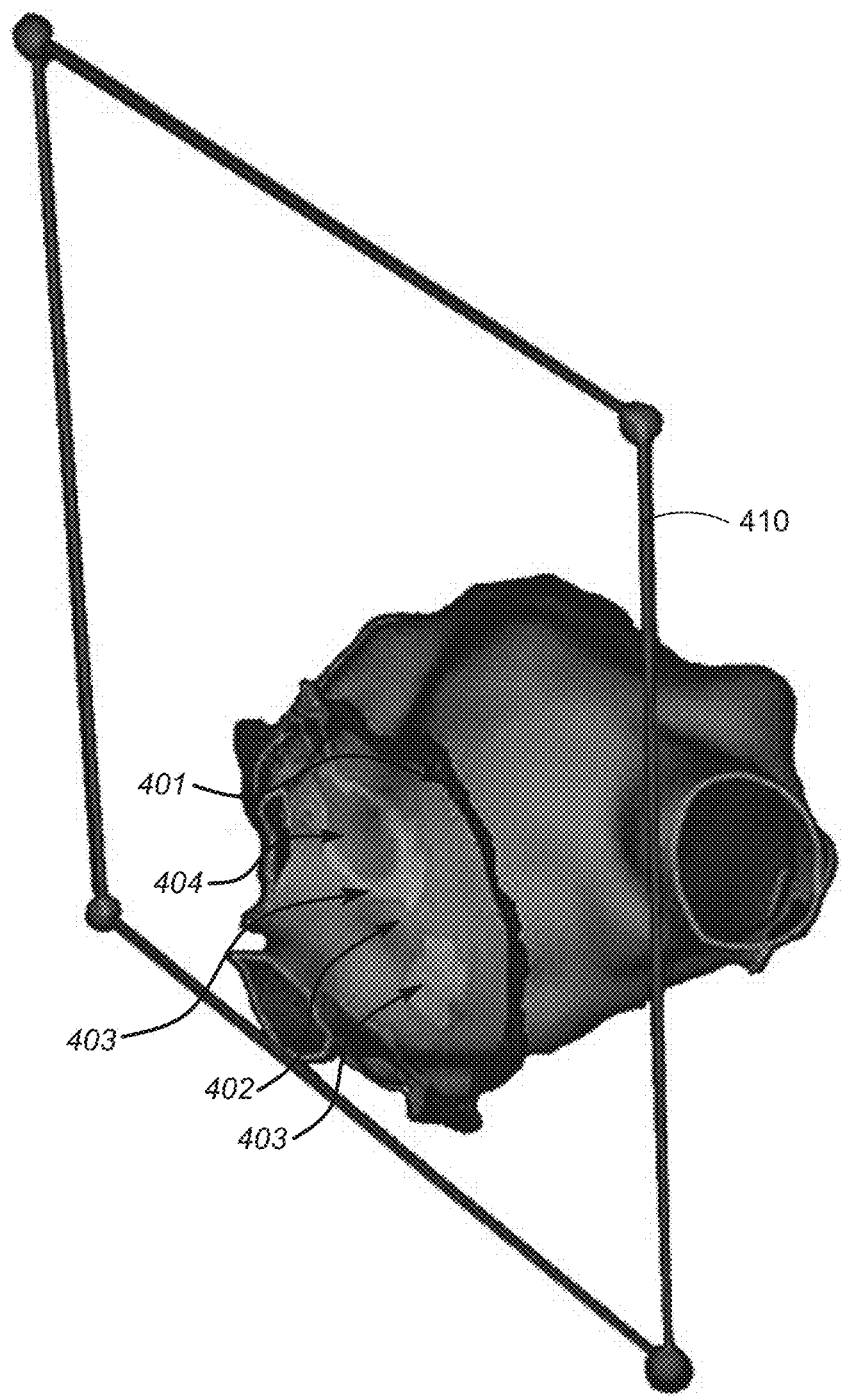
FIGS. 4A-4D are images of a voltage map shown from different perspectives, in accordance with embodiments of the present disclosure.
Figure 4B:
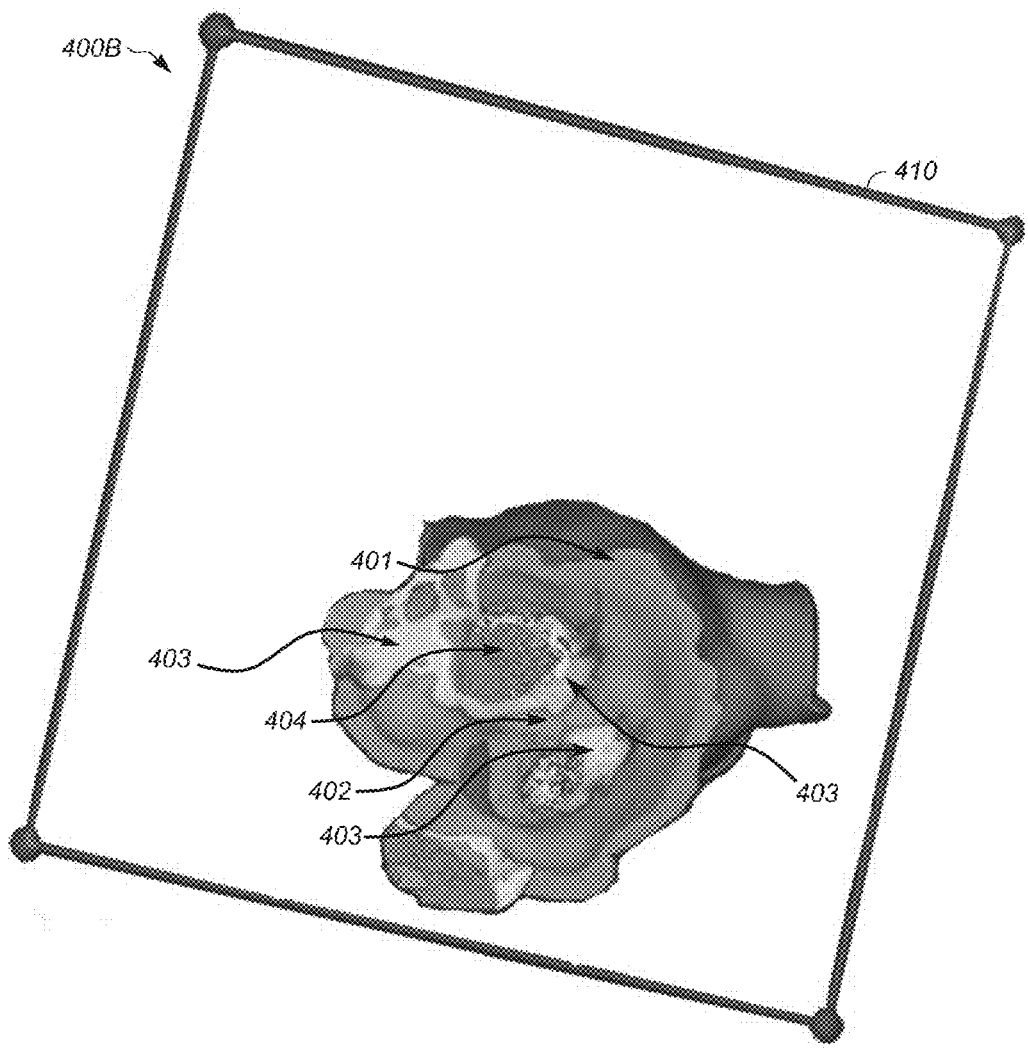
Figure 4C:
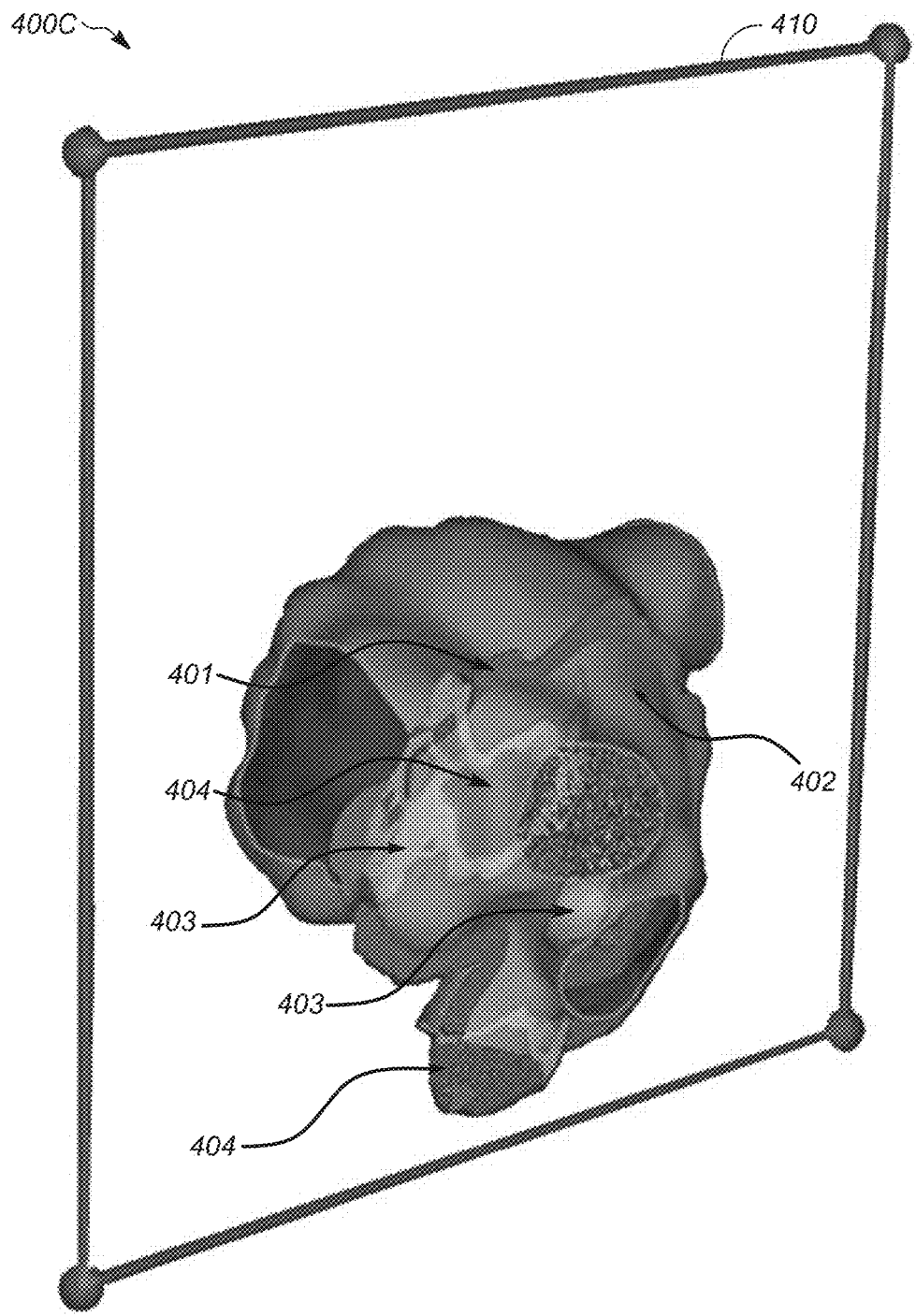
Figure 4D:
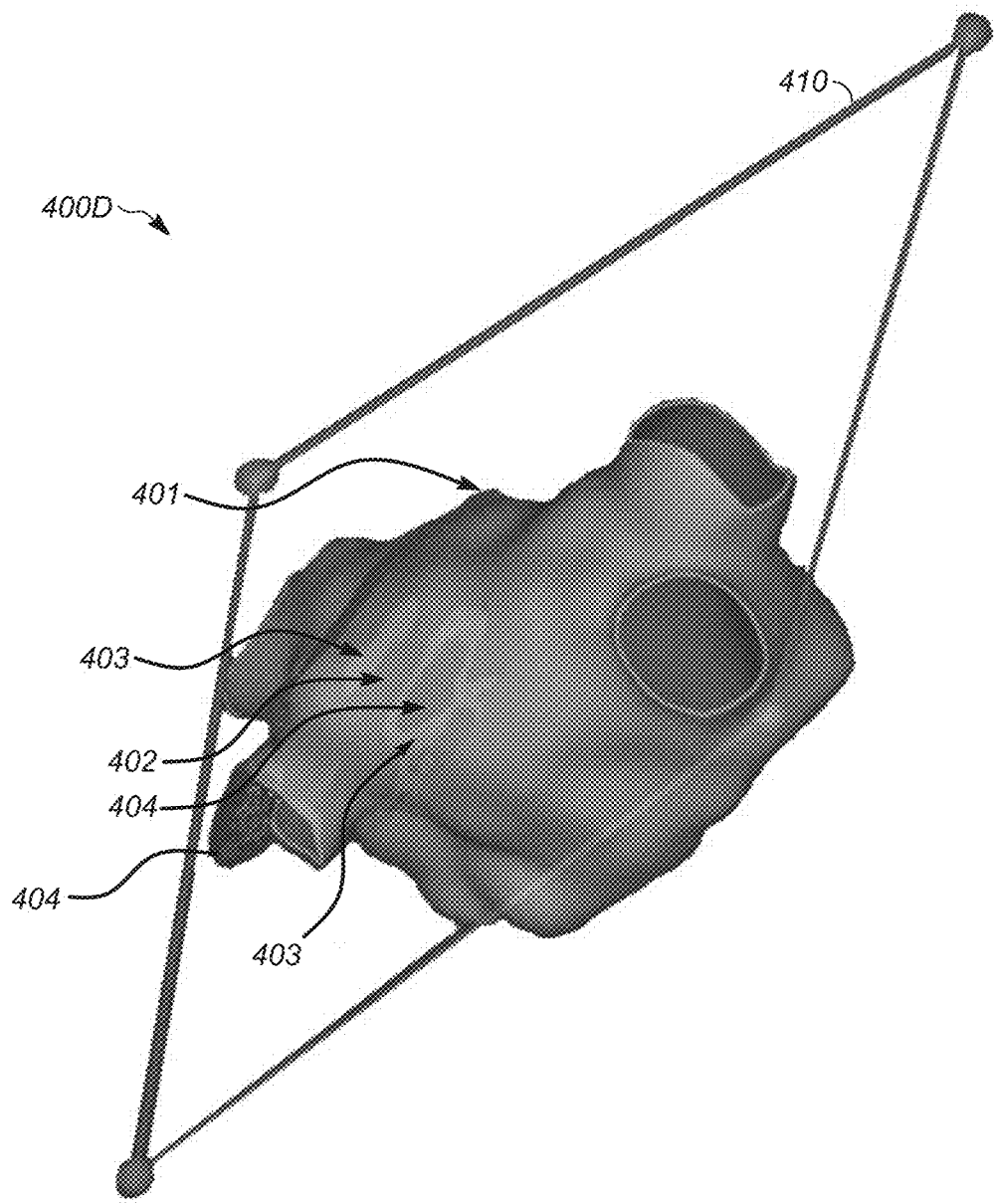

The first position of the surface map relative to the cardiac map can be any one of a number of different positions. For example, in embodiments, the first position of the surface map can dissect the cardiac map (as shown in FIGS. 4A-4B). The points where the surface map dissects the cardiac map can be different in different embodiments. As shown in FIGS. 4A and 4B, the position of the surface map relative to the cardiac map may be such that a part of the surface map is internal to the cardiac map and part of the surface map is external to the cardiac map. As another example, the surface map can have a first position relative to the cardiac map that is completely internal to the cardiac map. As even another example, the surface map can have a first position relative to the cardiac map that is completely external to the cardiac map. In some embodiments, the surface map can have a first position that is tangential to a surface of the cardiac map.

In embodiments, the first surface point can be located internal to (or below) the cardiac map, external to the cardiac map, and/or on the surface of the cardiac map. In embodiments where the first surface point is located internal to (or below) the cardiac map and/or external to the cardiac map, a cardiac electrical signal feature represented on the surface map may not be represented on the cardiac map. As such, the surface map may allow a user to view electrical activity that is captured by the system but not represented on the generated map, e.g., at points internal to and/or external to the cardiac map, which may, for example, facilitate detection of boundaries of internal structures and/or determine whether a structure not included in the cardiac map has contributed, or is contributing, to a cardiac disorder.

In embodiments where the first surface point is located internal to (or below) the cardiac map, a physician or other medical professional can determine whether an internal structure of the heart is the source of a cardiac disorder or is contributing to a cardiac disorder. Some examples of structures that may be internal to (or below) the endocardial surface of the heart include papillary muscles and septums. As an example, in some instances, a tachycardia can travel through a papillary muscle or a septum in the left atrium. In these cases, the generated surface map may be generated so that a first point of the surface map has a position that is within a predetermined threshold of the papillary muscle in which case electrical data can be represented on the surface map at the first surface point, as discussed below, to help determine whether the papillary muscle is contributing to the tachycardia.

In addition to, or alternatively to, viewing structures of a cardiac structure to diagnose or treat a cardiac disorder, a physician may also adjust the representation of cardiac structures to compensate for catheter-driven inaccuracies, such as tissue distention or "webbing," using the cardiac mapping systems described herein. For example, if a cardiac structure does not appear on the cardiac map, but is represented on a surface map having a first surface point that is located within a threshold distance of the cardiac structure, then a physician may modify the anatomical shell to include the cardiac structure.

In addition to generating a surface map having a corresponding first position relative to the cardiac map and including a first surface point, a first cardiac electrical signal feature is represented on the surface map at the first surface point if the first cardiac electrical signal is sensed at a point that is located within a threshold distance of the first surface point. That is, each cardiac electrical signal is sensed at a respective point; as such, if a first cardiac electrical signal is sensed at a point that is sufficiently close to the first surface point, then the first cardiac electrical signal feature can be represented on the surface map at the first surface point. The distance between the first surface point and the point at which the first cardiac electrical signal is sensed can be any type of distance between two points such as, for example, a rectilinear distance, L1, a Euclidean distance, L2, and/or the like. For example, if the distance between first surface point and the point at which the first cardiac electrical signal is sensed is a Euclidean distance, then the distance between the two points may be determined according to the following. Assume the surface map includes a first surface point that has coordinates $x_1$, $y_1$, $z_1$ and that a first cardiac electrical signal is sensed at a point with coordinates $x_2$, $y_2$, $z_2$. Further assume that a threshold distance is set to a millimeters. In this example, if $\sqrt{((x_1-x_2)^2+(y_1-y_2)^2+(z_1-z_2)^2)} \leq \alpha$ mm, then the first cardiac electrical signal feature can be represented on the surface map at the first surface point $(x_1, y_1, z_1)$. Examples of threshold distances include, but are not limited to, 0.01 mm, 0.05 mm, 0.1 mm, 0.5 mm and 1 mm.

The first cardiac electrical signal feature represented on the surface map may any be, or include, any features extracted from one or more corresponding sensed cardiac electrical signals and/or derived from one or more of such features. The first cardiac electrical signal feature may be represented on the surface map in a number of different ways. For example, the first cardiac electrical signal feature may be represented by a color, such that if the first cardiac electrical signal feature has an amplitude or other value within a first range then the first cardiac electrical signal feature may be represented by a first color, whereas if the first cardiac electrical signal feature has an amplitude or other value that is within a second range that is different than the first range, the first cardiac electrical may be represented by a second color. As another example, the first cardiac electrical signal feature may be represented by a number (e.g., a 0.2 mV sensed cardiac electrical signal feature can be represented by a 0.2 at its respective position on the surface map). Examples of a first cardiac electrical signal feature that can be represented at the first surface point include, but are not limited to, an activation time, a minimum voltage value, a maximum voltages value, a maximum negative time-derivative of voltage, an instantaneous potential, a voltage amplitude, a dominant frequency, a peak-to-peak voltage, and/or the like.

In embodiments, in addition to the first surface point, the surface map can include one or more other surface points. Additionally, a respective cardiac electrical signal feature can be represented on the surface map at a respective surface point of the one or more surface points if the respective cardiac electrical signal is sensed within a threshold distance of the respective surface point.

In embodiments, other features such as, for example, non-electrical signal features, non-cardiac electrical signal features, and/or the like, can be represented on a surface map at respective surface points. For instance, similar to cardiac electrical signal features, in embodiments, a non-electrical signal feature may be associated with a point in space and the non-electrical signal feature may be represented at a respective surface point if it is determined the respective point in space of the non-electrical signal feature is located within threshold distance of the respective surface point. Examples of non-electrical signal features include, but are not limited to, features derived from magnetic resonance imaging, a computerized tomography scan, ultrasonic imaging, and/or the like.

Embodiments of the method 300 also include displaying, on a display device, the cardiac map and the surface map, where the surface map is displayed at the first position (block 310). In embodiments, one or more display-enhancing functions may be performed to render the final cardiac map and/or surface map. When a certain number of display-enhancing functions (e.g., all available such functions, a certain set of functions, all functions available under the circumstances, and/or the like) are performed to render the cardiac map and/or the surface map, the cardiac map and/or the surface map may be displayed according to a first display mode, which may be referred to, for example, as "normal mode." If however, less than the certain number of display-enhancing functions (e.g., less than all of such functions, less than all of the available functions, and/or the like) are performed to render the cardiac map and/or the surface map, then the cardiac map and/or surface map may be displayed according to a second display mode, which may be referred to, for example, as "quick-view mode." The quick-view mode is described in more detail below in reference to block 316. In embodiments, the display-enhancing functions can smooth and/or sharpen the cardiac map and/or surface map to reduce noise and/or sharpen features therein. The display-enhancing functions that smooth and/or sharpen the cardiac map and/or surface map may include, but are not limited to, various linear and non-linear filtering functions, electrode position indicator, anatomical type projections (i.e., anatomical site tags).

In embodiments, the cardiac map may be displayed without the surface map. That is, for example, the surface map may be displayed with a cardiac map that is already displayed in response to a user input. The display device may have some or all of the same characteristics as the display device 40 discussed in FIG. 1. In embodiments, after the cardiac map and the surface map are displayed, the cardiac map and/or the surface map may be rotated, so that the cardiac map and/or the surface map may be viewed from different angles (see FIGS. 4A-4D for examples of this).

Embodiment of the method 300 may also include repositioning the surface map so that the repositioned surface map has a corresponding second position relative to the cardiac map, where the repositioned surface map includes a second surface point (block 312). Repositioning the surface map may include changing the orientation of the surface map and/or translating the surface map to another location while maintaining the same orientation. In embodiments, this can be useful if the first surface point is not within a threshold distance of a cardiac structure that a user is trying to examine. As such, the surface map can be repositioned so that the surface map includes a second surface point that is located within a threshold distance of a cardiac structure of interest.

The second position of the surface map may be any one of a number of different positions. For example, in embodiments, in the second position, the surface map may dissect the cardiac map (as shown in FIGS. 4A-4B). The points where the surface map dissects the cardiac map can be different in different embodiments. As another example, the surface map may have a second position that is completely internal to the cardiac map. As even another example, the surface map may have a second position that is completely external to the cardiac map. As another example, the surface map may have a second position that is tangential to a surface of the cardiac map.

Similar to the first surface point, in embodiments, the second surface point may be located internal to (or below) the cardiac map, external to the cardiac map, and/or on the surface of the cardiac map. In embodiments where the second surface point is located internal to (or below) the cardiac map and/or to external to the cardiac map, the cardiac electrical signal feature may not be represented on the cardiac map. As such, the surface map may allow a user to view electrical activity at points internal to and/or external to the cardiac map, which may help detect boundaries of internal structures and/or determine whether a structure not included in the cardiac map has contributed, or is contributing, to a cardiac disorder.

In embodiments, the surface map is repositioned to the second position in response to receiving a user input from a user. That is, for example, a user may be able to utilize an input device (e.g., a finger, a mouse, etc.) to reposition the surface map on the display device, thereby causing the surface map to be positioned at the second position. In embodiments, the second position is different than the first position and the second surface point does not have the same coordinates as the first surface point.

Similar to above, a second cardiac electrical signal feature of the plurality of cardiac electrical signal features may be represented on the repositioned surface map at the second surface point if a second cardiac electrical signal is sensed at a point that is located within a threshold distance of the second surface point. In embodiments, the second cardiac electrical signal feature may be different than the first cardiac electrical signal feature. The second cardiac electrical signal feature represented on the surface map may be any of the cardiac electrical signal features determined in block 304 above, and/or any features extracted and/or derived therefrom. Examples of a second cardiac electrical signal feature that may be represented at the second surface point include, but are not limited to, an activation time, a minimum voltage value, a maximum voltages value, a maximum negative time-derivative of voltage, an instantaneous potential, a voltage amplitude, a dominant frequency, a peak-to-peak voltage, and/or the like. Examples of threshold distances include, but are not limited to, 0.01 mm, 0.05 mm, 0.1 mm, 0.5 mm and 1 mm.

Similar to the first cardiac electrical signal feature, the second cardiac electrical signal feature may be represented on the surface map in a number of different ways. For example, the second cardiac electrical signal feature may be represented by a color, such that if the second cardiac electrical signal feature has an amplitude or other value within a first range then the second cardiac electrical signal feature may be represented by a first color, whereas if the second cardiac electrical signal feature has an amplitude or other value that is within a second range that is different than of the first range, the second cardiac electrical may be represented by a second color. As another example, the second cardiac electrical signal feature may be represented by a number (e.g., a 0.2 mV sensed cardiac electrical signal feature may be represented by a 0.2 at its respective position on the surface map).

In embodiments, in addition to the second surface point, the repositioned surface map may include one or more other surface points. Additionally, a respective cardiac electrical signal feature may be represented on the repositioned surface map at a respective surface point of the one or more surface points if the respective cardiac electrical signal is sensed within a threshold distance of the respective surface point.

Embodiments of the method 300 may also include displaying, on a display device, the cardiac map and the repositioned surface map at the second position (block 312). In embodiments, the cardiac map may be displayed without the repositioned surface map. That is, for example, the repositioned surface map may be displayed on a cardiac map that is already displayed, for example, in response to a user input. The display device may have some or all of the same characteristics as the display device 40 discussed in FIG. 1. In embodiments, after the cardiac map and the repositioned surface map are displayed, the cardiac map and/or the generated surface map may be rotated, so that the cardiac map and/or the surface map may be viewed from different angles.

In embodiments, the method 300 may further include performing less than all of a plurality of display enhancing functions to the displayed repositioned surface map if the displayed repositioned surface map is being viewed in a quick-view mode (block 314). As stated above, method 300 may include displaying the maps in a quick-view mode or a normal mode. In a normal mode a plurality of display enhancing functions may be performed to render the repositioned surface map. In a quick-view mode, less than the plurality of display enhancing functions may be performed to render the repositioned surface map. Examples of display enhancing functions may include, but are not limited to, linear and non-linear filtering functions, smoothing operations, interpolations, electrode position indicator, anatomical type projections and/or the like.

In embodiments, the quick-view mode may be automatically enabled when a particular condition is present and, likewise, switch back to normal view mode upon detecting another condition. For example, in embodiments, the method 300 may switch to quick view mode upon determining that the surface map is being repositioned, such as, for example, upon detecting motion of the surface map, receiving a user input indicating that the surface map is being repositioned (or will be repositioned), and/or the like. If one or more of these conditions are present, method 300 may include performing less than all of the display enhancing functions, which, in embodiments, may include not performing any display enhancing functions.

As another example, if the repositioned surface map has not been displayed at the second position for a threshold amount of time, then method 300 may include displaying the repositioned surface map in a quick-view mode. For example, once the repositioned surface map is displayed, method 300 may include starting a timer, so that at some time after the repositioned surface map is displayed, method 300 will be able to determine how long the repositioned surface map has been displayed. If the repositioned surface map has not been displayed for a period of time that exceeds the predetermined amount of time, method 300 may include performing less than all of the display enhancing functions, which, in embodiments, may include not performing any display enhancing functions. Examples of a predetermined amount of time can include, but is not limited to, 1 millisecond, 10 milliseconds, 100 millisecond and 1 second.

In embodiments, the system may switch back to normal mode upon determining that the repositioned surface map has been brought to rest at a new position, been at a new position for a predetermined amount of time and/or received a user input or an indication of a cessation of a user input (e.g., upon determining that a user has released a mouse button that had been depressed to affect a grab and drag operation on the surface map), and/or the like. As an example, if the repositioned surface map has been displayed for a period of time that exceeds the predetermined amount of time, method 300 may include performing a plurality of display enhancing functions. Examples of a predetermined amount of time can include, but is not limited to, 1 millisecond, 10 milliseconds, 100 millisecond and 1 second.

A quick-view mode can be helpful if the surface map is being repositioned by a physician that is searching a heart for any cardiac disorders using the surface map; and, as a result, a quick-view mode that does not perform additional display enhancing functions might help the physician to eliminate or focus in on some areas more quickly by repositioning the surface map in a somewhat fluid matter. Additionally, viewing the repositioned surface map in a quick-view mode can decrease the processing power required to reposition the surface map, while the physician is searching for any problematic areas.

As such, in embodiments where the repositioned surface map has been displayed for less than a predetermined amount of time, a less-refined representation of the repositioned surface map and any cardiac electrical signal features represented on the surface map at the second point may be displayed without performing any display enhancing functions or performing only a portion of the display enhancing functions (block 318). This less-refined representation is referred to herein as a quick-view mode.

Embodiments of the method 300 may also include displaying a virtual probe. A virtual probe may be used to inspect any of the cardiac electrical signal features and/or the corresponding cardiac electrical signals that were sensed by a mapping probe in block 302. To do so, the method may include positioning the virtual probe at one or more different positions on the cardiac and/or surface map, in response to receiving a user input. Examples of user input that may be indicative of positioning the virtual probe at a position include, but are not limited to, a single or double mouse click, a touch on a touchscreen, and/or the like. After the virtual probe is at a position, the method 300 may include repositioning the virtual probe to a different position on the cardiac map and/or the surface map, in response to receiving a user input. Examples of user input that may be indicative of repositioning the virtual probe to a different position include, but are not limited to, a mouse click and drag on the virtual probe and/or a touch and drag on the virtual probe.

In embodiments, the method 300 may include displaying an additional window on the display device. The additional window may facilitate displaying EGMs and/or features of cardiac electrical signals that were sensed at positions that are within a threshold distance of the position of the virtual probe's tip. Examples of electrical signals that may be displayed include, but are not limited to, a graph of the EGM waveform (which may include both bipolar and constituent unipolar EGMs) that was sensed by the mapping probe at a position closest to the position of the virtual probe's tip (referred to hereafter as "proximal EGM"), graphs of other EGMs sensed by the mapping probe (referred to hereafter as "distal EGMs") that are associated with the same beat as the beat associated with the proximal EGM, activation times of the proximal and distal EGMs, and fractionation indexes of the proximal and distal EGMs.

In embodiments, after the proximal and distal EGMs are displayed, the method 300 may include editing one or more of the cardiac electrical signal features in response to a user input and/or marking one or more of the cardiac electrical signal features in response to a user input. For example, the method 300 may include changing the activation times associated with the proximal and distal EGMs, in response to receiving a user input, in order to edit the activation map of the cardiac structure. As another example, the method 300 may include marking fractionated EGMs, in response to receiving a user input.

FIGS. 4A-4D are images 400A-400D of an illustrative map produced using aspects of embodiments of the system and methods of FIGS. 1 and 3. Each image 400A-400D of the exemplary map shown has the surface map 410. In a conventional voltage map, only the voltage on the endocardial surface of the one or more cardiac structures is viewable. Embodiments disclosed herein, however, include the surface map 410, which allows a user to view the voltages of structures external and internal to (or below) the endocardial surface of the one or more cardiac structures.

In each of the images 400A-400D, the surface map 410 is in the same first position relative to the cardiac map and includes the same first surface point 401. However, each of the images 400A-400D are rotated to show that the cardiac map and the surface map 410 can be viewed from different angles, as described above in FIG. 3. In addition to the first surface point 401, the surface map 410 includes other surface points 402, 403, 404 as well. The other surface points 402, 403, 404 include representations of features of cardiac electrical signals sensed at respective points located within threshold distances of the other surface points 402, 403, 404.

The cardiac electrical signal feature in this illustrative embodiment is voltage. Thus, the cardiac map shown in FIGS. 4A-4D is a voltage map and shows the magnitude of voltages at different points on the cardiac map. More specifically, the first surface point 401, the second surface point 402, the third surface point 403 and the fourth surface point 404 of FIGS. 4A-4D have respective voltage magnitudes. In healthy areas of the myocardium of a cardiac structure, the voltage is higher than unhealthy areas of the myocardium of a cardiac structure and inside the blood pool.

In FIGS. 4A-4D The first surface point 401 has a higher voltage magnitude than the second surface point 402; the second surface point has a higher voltage magnitude than the third surface point 403; and the third surface point 403 has a higher voltage magnitude than the fourth surface point 404. The first surface point 401 has a location near the endocardial surface of the one or more cardiac structures. The fourth surface point 404 has a location in the blood pool of the one or more cardiac structures. Since the fourth surface point 404 does not correspond to myocardium, the low voltage magnitude may not be a concern for a physician. The second surface point 402 (also referred to herein as septum 402) that connects the two pulmonary veins, however, may be a concern for a physician if the septum 402 had aberrant activation times. This septum 402 is not viewable using conventional methods. Here, however, since the voltage of points internal to the one or more cardiac structures are displayed on the surface map 410, a physician can determine whether the septum 402 is inappropriately mapped by determining whether the septum 402 is displaying an abnormally low voltage magnitude. If the septum 402 is displaying an abnormally low voltage magnitude, a physical may modify the map until the septum 402 is displaying an appropriate voltage magnitude. After the map is modified, a physician may be able to better diagnose any aberrant activation times of the septum 402.

Various modifications and additions can be made to the exemplary embodiments discussed without departing from the scope of the present disclosure. For example, while the embodiments described above refer to particular features, the scope of this disclosure also includes embodiments having different combinations of features and embodiments that do not include all of the described features. Accordingly, the scope of the present disclosure is intended to embrace all such alternatives, modifications, and variations as fall within the scope of the claims, together with all equivalents thereof.

We claim:

1. A method for mapping and displaying internal cardiac structures, the method comprising:
   sensing, using a mapping probe, a plurality of cardiac electrical signals at a plurality of points;
   generating, using a processing device, a cardiac map of at least a portion of one or more cardiac structures based on at least a portion of the plurality of cardiac electrical signals;
   generating, using the processing device, a repositionable surface map having a first position relative to the cardiac map;
   displaying, on a display device, the cardiac map;
   displaying, on the display device, the repositionable surface map at the first position;
   receiving, via a user input device, a user input to reposition the repositionable surface map to a second position; and
   displaying, on the display device, the repositionable surface map at the second position in response to the user input.

2. The method of claim 1, the repositionable surface map comprising a first surface point, wherein sensing the plurality of cardiac electrical signals at the plurality of points comprises sensing a first cardiac electrical signal feature of a first cardiac electrical signal of the plurality of cardiac electrical signals at a point that is located within a threshold distance of the first surface point; and the method further comprising displaying the first cardiac electrical signal feature on the repositionable surface map at the first surface point.

3. The method of claim 2, wherein the first surface point is not located on the cardiac map.

4. The method of claim 2, wherein the first cardiac electrical signal feature is not represented on the cardiac map.

5. The method of claim 2, wherein the first cardiac electrical signal feature comprises at least one of: an activation time, a minimum voltage value, a maximum voltages value, a maximum negative time-derivative of voltage, an instantaneous potential, a voltage amplitude, a dominant frequency, and a peak-to-peak voltage.

6. The method of claim 2, the repositionable surface map comprising a second surface point, wherein sensing the plurality of cardiac electrical signals at the plurality of points comprises sensing a second cardiac electrical signal feature of a second cardiac electrical signal of the plurality of cardiac electrical signals is sensed at a point that is located within a threshold distance of the second surface point; and the method further comprising displaying the second cardiac electrical signal feature at the second surface point.

7. The method of claim 1, wherein the repositionable surface map is a plane map.

8. The method of claim 1, further comprising: receiving a signal to view the repositionable surface map in a quick-view mode and performing less than all of a plurality of display-enhancing functions to render the repositioned surface map in the quick-view mode.

9. The method of claim 1, wherein the repositionable surface map passes through a papillary muscle or a septum of the one or more cardiac structures.

* * * * *